United States Patent [19]

Reymond et al.

[11] Patent Number: 5,576,174
[45] Date of Patent: Nov. 19, 1996

[54] CATALYTIC ANTIBODY WITH PRIMARY AMINE COFACTOR

[75] Inventors: Jean-Louis Reymond, Del Mar; Yuanwei Chen, San Diego, both of Calif.

[73] Assignee: The Scripps Research Institute, La Jolla, Calif.

[21] Appl. No.: 417,370

[22] Filed: Apr. 5, 1995

[51] Int. Cl.$^6$ .............................. C12Q 1/25; C12N 9/00
[52] U.S. Cl. .............................. 435/4; 435/188.5
[58] Field of Search ...................... 435/188.5, 4

[56] References Cited

U.S. PATENT DOCUMENTS 5,500,358  3/1996  Reymond et al. .............. 435/188.5

OTHER PUBLICATIONS

Jahangiri, G. K., et al. (1994) J. Am. Chem. Soc. 116(25), 11264–11274.
Koch, T., et al. (1995) J. Am. Chem. Soc. 117(37), 9383–9387.
Wagner, J., et al. (1995) Science 270, 1797–1800.
Hupe et al. *Enzyme Mechanisms*, Ed. M. I. Page and A. Williams, 1987, pp. 317–344.
Fessner et al. *Kontakte* (vol. 3), 3–9 (1992).
Hupe et al. New Comprehensive Biochemistry, vol. 6, The Chemistry of Enzyme Action, Ed. M. I. Page, Elsevier, Amsterdam, 1984, Chapter 8, pp. 271–301.
Johnsson et al. *Nature*, 365, p. 530 (1993).
Reymond et al. Angew. Chem. Intl. 30, 1711, (1991).
Reymond et al. J. Am. Chem. Soc. 114, 2257 (1992).
Reymond et al. Angew. Chem. Intl. 33, 475 (1994).
Reymond et al. J. Am. Chem. Soc. 115, 3909 (1993).

*Primary Examiner*—Charles L. Patterson, Jr.
*Attorney, Agent, or Firm*—Donald G. Lewis

[57] ABSTRACT

Antibodies raised against the quaternary piperidinium haptens are shown to catalyze the aldol stereoselective addition of acetone to aldehydes using the primary benzylamine as a cofactor.

10 Claims, 4 Drawing Sheets

CATALYTIC ANTIBODY WITH PRIMARY AMINE COFACTOR

GOVERNMENT RIGHTS

This invention was made, in part, with Government Support under Grant No. GM 49736 from the National Institutes of Health. The U.S. government hay have certain rights in this invention.

FIELD OF INVENTION

The invention relates to catalytic antibody having aldolase activity. More particularly the invention relates to catalytic antibody which employs a primary amine as a cofactor in the catalysis of the aldol addition reaction.

BACKGROUND

Catalytic antibody technology can often provide a rapid and versatile entry into new catalytic proteins. (R. A. Lerner, et al., *Science* (1991): vol. 252, pp 659–667; and P. G. Schultz, et al., *Acc. Chem. Res.* (1993), vol. 26, pp 391.) A number of enzymatic processes have been successfully mimicked by catalytic antibodies. Tramontano and others have shown that catalytic antibody can be generated which have hydrolase activity with respect to ester bonds. (A. Tramontano et al., *J. Am. Chem. Soc.* (1988): vol. 110, pp 2282; K. D. Janda et al., *Science* (1989): vol. 244, pp 437; J. Guo et al., *J. Am. Chem. Soc.* (1994): vol. 116, pp 6062; and G. W. Zhou, et al., *Science* (1994): vol. 265, pp 1059.) Similarly, Janda and others have shown that catalytic antibody can be generated which have hydrolase activity with respect to amide bonds. (K. D. Janda et al., *Science* (1988): vol. 241, pp 1188; and M. T. Martin et al., *J. Am. Chem. Soc.* (1994): vol. 116, pp 6508.) Catalytic antibodies having hydrolytic activity with respect to a variety of glycosidic bonds have also been generated. (J. L. Reymond et al., *Angew. Chem. Int. Ed. Engl.* (1991): vol. 30, pp 1711; and J. Yu, et al. *Angew. Chem. Int. Ed. Engl.* (1994): vol. 33, pp 339.) Catalytic antibodies having the ability to form amide bonds have been generated by several investigators. (S. J. Benkovic et al., *Proc. Natl. Acad. Sci. USA* (1988): vol. 85, pp 5355; J. R. Jacobsen et al., *Science* (1992): vol. 256, pp 365; R. A. Gibbs et al. *Science* (1992): vol. 258, pp 803; ; R. Hirschmann et al., *Science* (1994): vol. 265, pp 234; and J. R. Jacobsen et al., *Proc. Natl. Acad. Sci. USA* (1994): vol. 91, pp 5888.) Decarboxylation reactions can be catalyzed using catalytic antibody generated for that purpose. (C. Lewis et al., *Science* (1991): vol. 253, pp 1019; J. A. Ashley et al., *J. Am. Chem. Soc.* (1993): vol. 115, pp 2515; and T. M. Tarasow et al., *J. Am. Chem. Soc.* (1994): vol. 116, pp 7959.) The heme-mediated reduction of hydrogen peroxide can be catalyzed using catalytic antibody (A. G. Cochran et al., *J. Am. Chem. Soc.* (1990): vol. 112, pp 9414.) The 3,3-sigmatropic rearrangement catalyzed by chorismate mutase can also be catalyzed by catalytic antibody. (D. Y. Jackson et al., *J. Am. Chem. Soc.* (1988): vol. 110, pp 4841; D. Hilvert et al., *J. Am. Chem. Soc.* (1988): vol. 110, pp 5593; D. Y. Jackson et al., *Angew. Chem. Int. Ed. Engl.* (1992): vol. 31, pp 182; and M. R. Haynes et al., *Science* (1994): vol. 263, pp 646.) The imitation of natural enzymes by catalytic antibodies is a continuing challenge as well as a source of inspiration in this field.

Many enzymes rely on imine and enamine intermediates to catalyze exchange reactions at the α-carbon of carbonyl compounds. Aldolases catalyze the aldol addition of ketones with aldehydes and decarboxylases catalyze the decarboxylation of β-keto acids. The catalytic group in both enzymes is the ε-amino-group of a lysine residue. A related reaction is the interconversion of α-keto and α-amino acids catalyzed by transaminases using the cofactor pyridoxamine phosphate. The catalytic mechanisms of each of these reactions are reviewed by D. J. Hupe, *Enzyme Mechanisms*, Ed. M. I. Page and A. Williams, 1987, p. 317–344 and by W.-D. Fessner, *Kontakte* (1992): vol. 3, pp 3–9.

The mechanism of these reactions, illustrated below for aldolases (scheme 1), involves initial condensation of a carbonyl group of the substrate with the amine to form an iminium intermediate I. The iminium cation is the protonated form of the imine. Both forms are in rapid equilibrium and their relative proportions depends on the pH. The iminium is the kinetically relevant form. When employed herein, the term iminium generally refers to both forms. This intermediate then undergoes an exchange at the α-carbon of the carbonyl, a process which is facilitated by formation of enamine II. In the aldolase reaction, a proton is exchanged for an aldehyde, with formation of a new carbon-carbon bond. Finally, hydrolysis of the primary adduct liberates the carbonyl product and regenerates the free amino group, e.g., D. J. Hupe, in *New Comprehensive Biochemistry*, vol. 6, *The Chemistry of Enzyme Action*, Ed. M. I. Page, Elsevier, Amsterdam, 1984, chapter 8.

All of these reactions play central roles in biosynthetic pathways, including the biosynthesis, interconversion and degradation of sugars and amino-acids. The ability to mimic these processes using catalytic antibodies would offer significant opportunities for designing synthetically useful catalytic reactions. What is needed is a catalytic antibody directed to catalyzing aldol reactions using enamine chemistry, i.e., utilizing a primary amine as cofactor in a catalytic process as employed by aldolase enzymes.

Scheme 1.
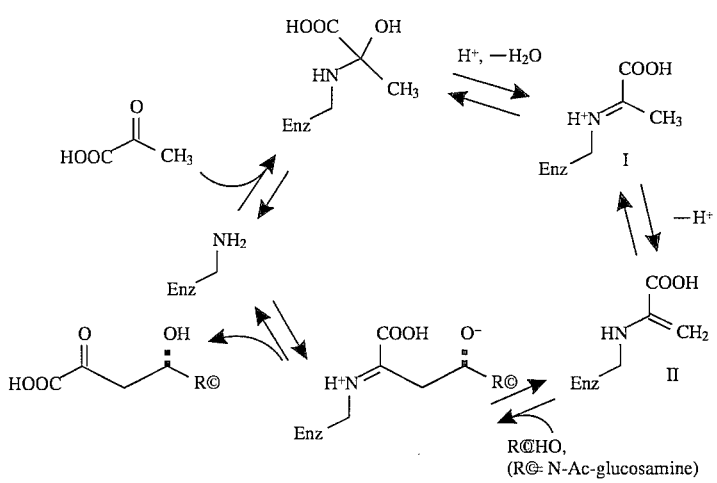
Catalytic mechanism for aldolases of type I at the example of N-Acetylneuraminic acid aldolase (EC 4.1.3.3).
Scheme 2.
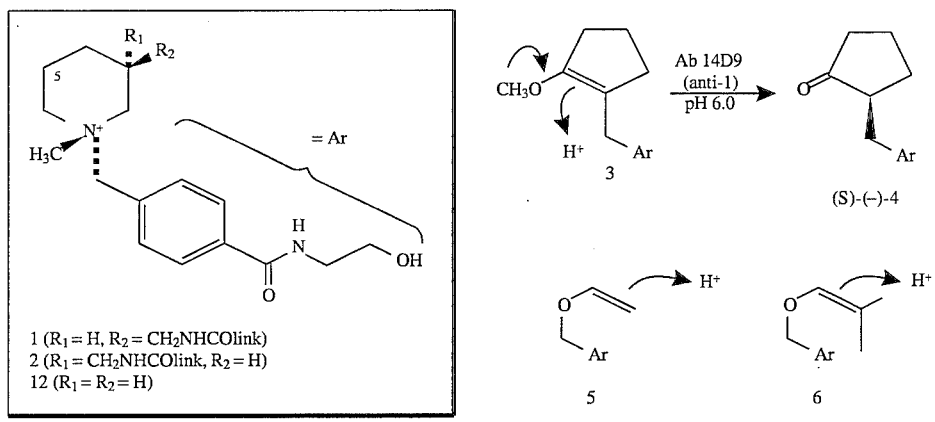
Antibodies raised against haptens 1 and 2 catalyze the hydrolysis of enol ethers 3, 5 and 6.
Scheme 3.
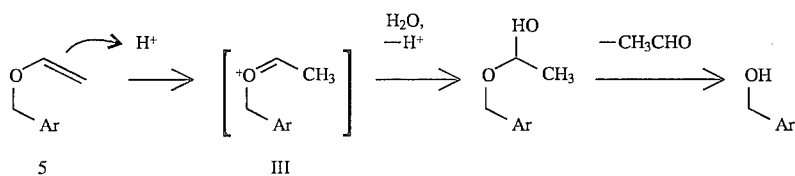

-continued
Scheme 3.

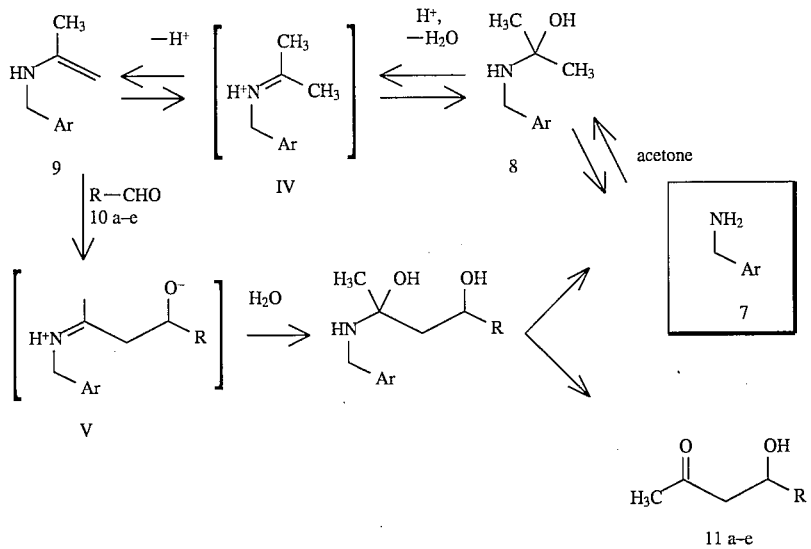

Catalytic, enamine mediated aldolization cycle and related hydolysis of enol ethers.

SUMMARY

Antibodies raised against the quaternary piperidinium haptens 1 and 2 are shown to catalyze the aldol addition of acetone to aldehydes using the primary benzylamine 7 as cofactor. The reaction shares some similarity with aldolase enzymes in which the ε-amino group of a lysine residue is the catalytic group. The aldolization cycle incorporates enamine 9 as a key intermediate, and is both structurally and mechanistically closely related to the hydrolysis of enol ethers 5 and 6, which is also catalyzed by antibodies against the same haptens. The absolute configuration of the chiral center formed in the aldolization catalyzed by antibody 72D4 (anti-2) is controlled by the antibody. The condensation of acetone and amine 7 to iminium IV, the direct precursor of enamine 9, can be followed by formation of an α-aminonitrile 17 in the presence of cyanide, and is catalyzed by antibody 72D4. The rate determining step is the coupling of enamine 9 with the aldehyde leading to iminium V. Catalysis is probably achieved by electrostatic complementarity to the transition state, and by binding to acetone and amine 7. The amine condenses with the aldehyde in solution to form the catalytically non-productive imine 16 ($K_{16}$=7.8 mM). Formation of this imine within the antibody binding site probably accounts for the apparent binding observed with the different aldehyde substrates 10a–10e. The key primary amine 7 is regenerated at the end of the cycle and operates as a cofactor. The process can be adapted for generating and identifying catalytic antibodies for a number of aldol type processes.

The antibody-catalyzed aldol reaction is disclosed to proceed by the pathway illustrated in scheme 3. For aldolase enzymes, catalysis may be explained in part by the simple presence of a primary amine residue of unusually low pK, within the active site. K. Johnsson et al. has used this principle to

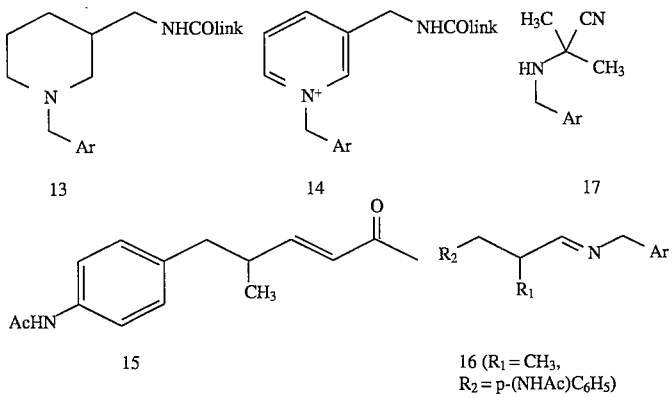

design catalytic peptides having aldolase activity. (K. Johnsson et al., Nature (1993): vol. 365, pp 530.) The invention disclosed herein is conceptually different because the protein catalyst has to compete with the free cofactor in solution, which by itself already possesses this key primary amino group of low $p_a$ ($pK_a(7)$=8.5). Factors responsible for a specific activation of amine 7 for aldolization upon binding to the antibody can be identified to account for the catalysis. These factors serve to lower the energy of the transition state for the rate determining step, which is disclosed herein to be the aldol addition of enamine 9 to the aldehyde. This transition state can be approximated by intermediate V (scheme 3).

The rate determining step, which is the carbon-carbon bond formation, also induces chirality. The enantioselectivity observed in the antibody-catalyzed reaction confirms that it takes place in the chiral environment of the antibody binding site, rather than in solution, which must be the case for the antibody to catalyze the reaction. As discussed for the reaction design, the antibody binding pocket induced by hapten 2 should provide electrostatic stabilization for iminium V, and might also facilitate the formation of intermediate IV.

Formation of the transition state of aldol coupling formally represents a trimolecular condensation between amine 7, acetone, and the aldehyde. Antibody binding to these individual species should promote this condensation within the active site and appear as catalysis. Such a mechanism is especially attractive because antibodies are primarily binding proteins.

Binding could contribute directly to catalysis by promoting the condensation of the cofactor 7 with acetone, an effect which could also account for the catalysis observed for the formation of aminonitrile 17. A binding site for the cofactor ($K_M(7)$=95 mM at pH 9.0) is provided by antibody complementarity to the aromatic nucleus (Ar) of hapten 2. Binding of acetone in a geometry suitable for iminium IV and enamine 9 might be achieved by a hydrophobic interaction between one of its methyl groups and the antibody site complementary to the methylene in position 5 of the piperidine ring in hapten 2 (scheme 2). Antibody 72D4 binds acetone relatively weakly in absolute terms ($K_M$ (acetone)= 120 mM at pH 9.0), and recognition of a single methyl group could be sufficient to account for this effect.

The active sites of anti-1 and anti-2 antibodies are relatively hydrophobic. Considering that the condensation of amine 7 with acetone, to form iminiums IV and V, releases a molecule of $H_2O$, exclusion of water from the active site by a medium effect should contribute to catalysis by shifting this condensation equilibrium to the transition state even further than the effect of simple substrate binding.

Antibody binding to the aldehyde could also enhance catalysis by favoring the aldol coupling of the antibody-bound enamine over its hydrolysis. However, such an effect would require a specific binding site for the aldehyde substrate. An inspection of the hapten structure, together with the relatively broad substrate tolerance and lack of efficient kinetic resolution of aldehyde 10a by the antibody, suggests that a specific aldehyde binding site does not exist (see below).

Binding selectivity and catalysis

The equilibrium condensation of cofactor 7 with acetone is extremely unfavorable. The observation that it remains undetected at 20% v/v (1.4M) by $^1$H-NMR sets a lower limit of 20M for the dissociation constant of the conjugate base of iminium IV to acetone and amine 7. By contrast, the condensation of the amine with the aldehyde to form the catalytically unproductive imine 16 takes place readily ($K_{16}$=7.8 mM, FIG. 3). The efficiency of the antibody catalyzed aldol reaction should be strongly influenced by the ability to promote the disfavored, yet catalytically productive, condensation of amine 7 with acetone, over the more likely formation of imine 16. This selectivity might not be completely achieved by antibody 72D4. We propose that the Michaelis-Menten constants of the aldehydes reflect competitive inhibition by their imines (e.g. 16), and that productive aldehyde binding at the transition state is minimal. This can account both for the structural tolerance and for the apparent binding with these substrates. The catalytic efficiency of the antibody with each aldehyde would depend on the relative potency of inhibition by the corresponding imine. In that respect, it is interesting to note that aldolase enzymes are usually very selective for the ketone, but can display a very broad substrate tolerance for aldehydes. These enzymes might have optimized this type of binding selectivity to perfection to achieve efficient catalysis.

Catalysis is disclosed to arise from a specific activation of the primary amine cofactor 7 within the antibody combining site of anti-1,2 antibodies, a phenomenon that cannot not be ascribed to non-specific interactions with the antibody as it was not observed with a number of control proteins, including antibodies to closely related haptens. An antibody catalyzed stereoselective aldol reaction, which represents the first case of an antibody-catalyzed bimolecular carbon-carbon bond formation other than the Dieis-Alder reaction.

The reaction follows an enamine mechanism similar to the enzymatic aldol reaction catalyzed by type I aldolases. The rate determining step is the aldol coupling itself, and its catalysis by antibody 72D4 is probably achieved by electrostatic complementarity to the transition state as well as selective binding to amine 7 and acetone. Competitive inhibition by imine 16, formed by condensation of the cofactor with the aldehyde, might account for apparent binding of the aldehydes in the absence of binding site for these substrates.

It is noteworthy that amine 7, which is recognized by the antibody, is not consumed in the reaction cycle. This cofactor assisted system should in principle allow for a broad substrate tolerance and avoid product inhibition, and could lead to useful catalysts for a number of aldol type reactions. A further advantage of amine catalysis is that the enolization of the ketone, to form the enamine intermediate 9, is also catalytic, so that the overall aldol coupling can be done in one step. The present system thus follows an entirely catalytic route for the aldol reaction, which would not have been the case using a Mukaiyama coupling of our enol ethers.

Successful design strategies leading to catalytic antibodies include matching the structure of the hapten with the transition state (structure to structure), and placing an electric charge in the hapten where acid-base catalysis is desired (structure to mechanism). This is possible because the antibody binding pocket is induced in real time by the experimenter. Here we followed a new strategy based on a mechanistic analogy between a known reaction, the hydrolysis of enol ethers, and the desired, enamine mediated, aldol reaction (mechanism to mechanism). It should be noted that the monoclonal antibodies catalyzing this aldol reaction were different from those catalyzing the enol ether hydrolysis reaction used as a mechanistic guide. Nevertheless, the number of catalytic antibodies obtained (6 out of 46) is comparable to what is usually obtained in immunization experiments with structure based hapten design. Therefore, this approach should clearly be useful for expanding the catalytic repertoire of existing antibodies to new reactions.

One aspect of the invention is directed to a method for catalyzing a stereoselective aldol addition reaction between a ketone and an aldehyde. The method comprises the step of admixing the ketone and the aldehyde in a solution containing a catalytic amount of a catalytic antibody and a cofactor. The cofactor is a primary or secondary amine having a $pK_a$ substantially equivalent to or lower than the $pK_a$ of benzylamine. A preferred primary or secondary amine is benzylamine. A preferred catalytic antibody has an epitope that binds a quaternary piperidinium hapten. A preferred ketone is acetone.

Another aspect of the invention is directed to a catalytically active mixture which comprises a catalytic antibody or antibody fragment and a primary or secondary amine cofactor admixed within a solvent. The catalytic antibody is of a type which has a catalytic activity directed to catalyzing a stereoselective aldolization reaction. However, the activity of the catalytic antibody is dependent upon the presence the primary or secondary amine cofactor.

Another aspect of the invention is directed to a reaction mixture. The reaction mixture comprises a catalytic antibody or antibody fragment, a primary or secondary amine cofactor, a ketone, and an aldehyde. All components are admixed with a solvent. The catalytic antibody has a catalytic activity for catalyzing a stereoselective aldolization reaction between the ketone and the aldehyde dependent upon the presence the primary or secondary amine cofactor.

Another aspect of the invention is directed to a method for identifying a catalytic antibody having a catalytic activity dependent upon a primary or secondary amine cofactor. The method includes the steps of admixing the catalytic antibody and one or more substrates with or without the primary or secondary amine cofactor. The two admixtures are then monitored with respect to the rate of conversion of substrate to product. The rates of conversion are compared for the two admixtures and catalytic antibody having a greater rate of a conversion of substrate to product with cofactor as compared to the rate without cofactor is identified as catalytic activity dependent upon such primary or secondary amine cofactor.

Another aspect of the invention is directed to a method for catalyzing an aldol addition reaction between a ketone and an aldehyde without a catalytic antibody. The aldol addition reaction is catalyzed in an acidic solution by the addition of a catalytic amount of primary amine cofactor. The primary amine cofactor has a $pK_a$ substantially equivalent to or lower than the $pK_a$ of benzylamine for catalyzing the aldol addition reaction and is non-proteinaceous.

Figure 1:
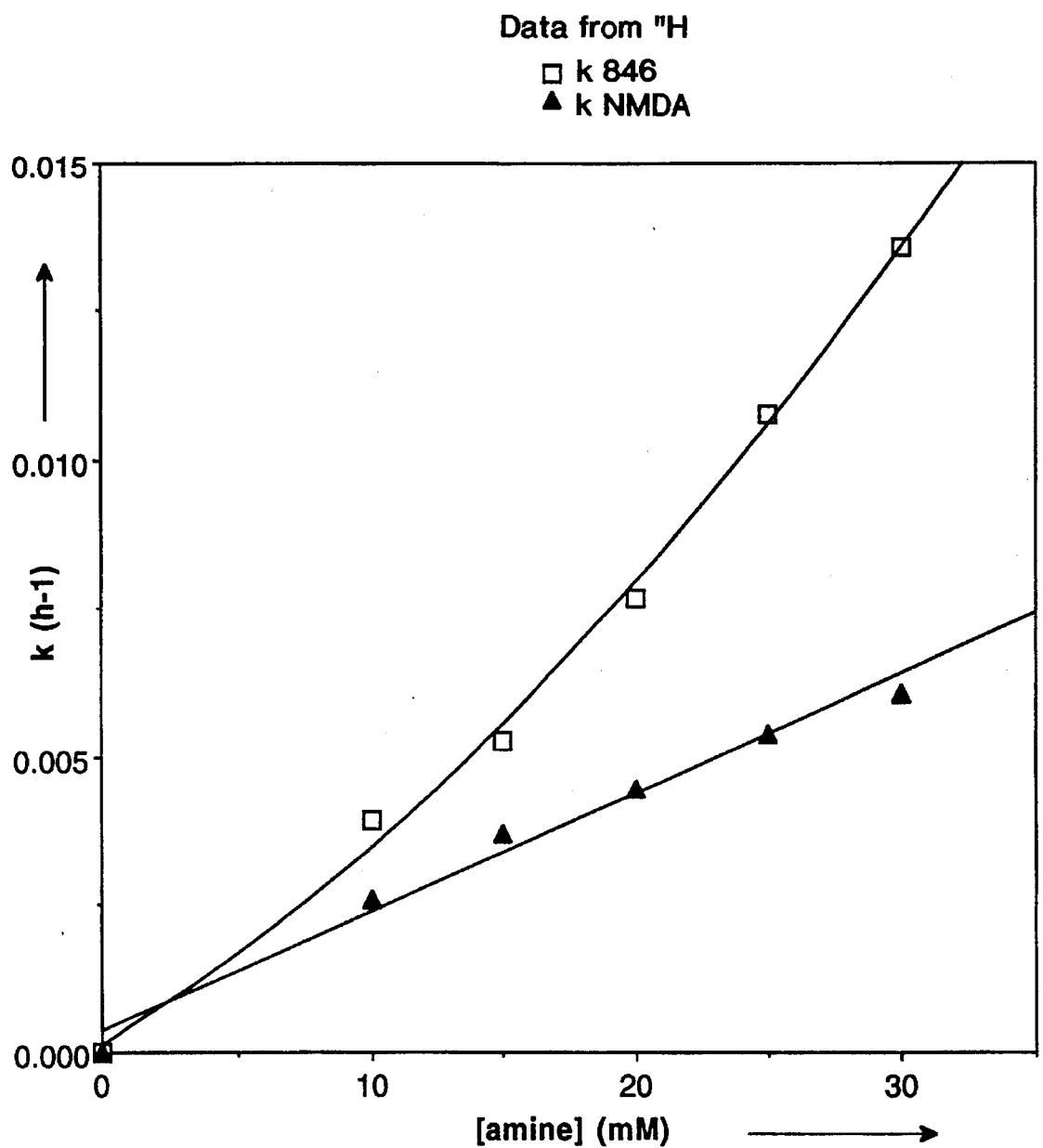
FIG. 1 illustrates the comparative kinetics of the aldol reaction of 10a and acetone to produce 11a using amine 7 as a catalytic agent and using hydroxide catalysis.

Scheme 4.

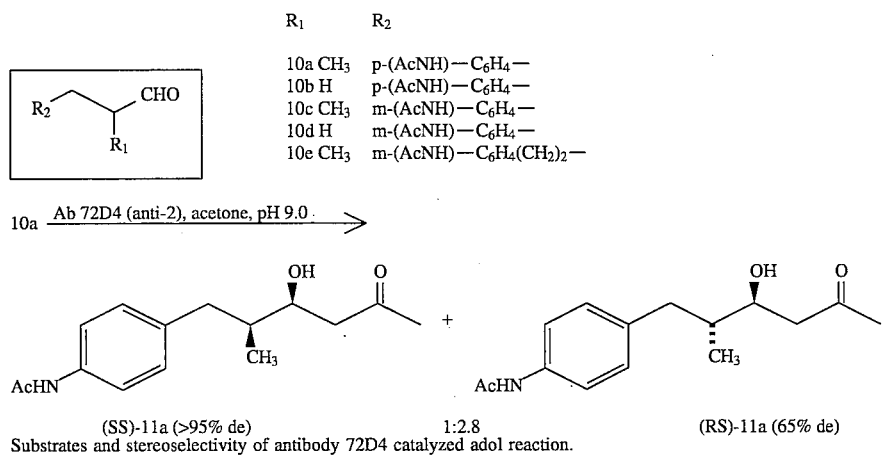

| | R₁ | R₂ |
|---|---|---|
| 10a | CH₃ | p-(AcNH)—C₆H₄— |
| 10b | H | p-(AcNH)—C₆H₄— |
| 10c | CH₃ | m-(AcNH)—C₆H₄— |
| 10d | H | m-(AcNH)—C₆H₄— |
| 10e | CH₃ | m-(AcNH)—C₆H₄(CH₂)₂— |

10a →(Ab 72D4 (anti-2), acetone, pH 9.0)→ (SS)-11a (>95% de) + (RS)-11a (65% de)   1:2.8

Substrates and stereoselectivity of antibody 72D4 catalyzed adol reaction.

DETAILED DESCRIPTION

Design of the Catalytic Cycle

Antibodies against haptens 1 and 2 are reported by J.-L. Reymond et al. to catalyze the enantioselective protonation of prochiral enol ethers (e.g. 3) to produce optically pure carbonyl compounds. (J.-L. Reymond et al., *Angew. Chem. Int. Ed. Engl.* (1991): vol. 30, pp 1711; J.-L. Reymond et al., *J. Am. Chem. Soc.* (1992): vol. 114, pp 2257; and J.-L. Reymond et al., *Angew. Chem. Int. Ed. Engl.* (1994): vol. 33, pp 475.) This rection enables the prepartion of ketone (S)–(–)-4 on the gram scale (scheme 2). It is disclosed herein that these antibodies can also serve as useful synthetic catalysts with respect to the coupling of the enol derivative with an electrophile other than the proton, for example an aldehyde. This leads to a carbon-carbon bond forming aldol reaction.

Initial experiments aimed at the direct coupling of these enol ethers with aldehydes, in analogy to the Mukaiyama aldol reaction, were not successful. (T. Mukaiyama et al., *J. Am. Chem. Soc.* (1974): vol. 96, pp 7503.) Similar experiments directed to aldol reactions of silyl enol ethers in water are disclosed by Lubineau. (A. Lubineau et al., *Tetrahedron* (1988): vol. 44, pp 6065.)

It is disclosed herein that anti-1,2 antibodies can be employed with respect to aldolization catalysis by the enzymatic mechanism (scheme 1) if an enamine intermediate related to the enol ether substrates is provided within the reaction cycle. We observed that enol ethers and enamines have very similar structures and reactivities and that some of the anti-1,2 antibodies catalyzed the hydrolysis of enol ethers 5 and 6 (scheme 2). (J.-L. Reymond et al., *J. Am. Chem. Soc.* (1993): vol. 115, pp 3909; and G. K. Jahangiri et al., *J. Am. Chem. Soc.* 1994, in press.) Accordingly, we disclose herein that the anti-1,2 antibodies can also catalyze an aldolization cycle if the related enamine 9 is provided as a cofactor the the reaction, derived from the benzylic amine 7 (scheme 3).

Catalysis for the hydrolysis of enol ethers 5 and 6 involves stabilization of the transition state of highest energy, which can be approximated by oxocarbonium ion III. (A. J. Kresge et al., *J. Chem. Soc. B,* (1967): vol. 53, pp 58; and A. J. Kresge et al., *J. Am. Chem. Soc.* (1992): vol. 114, pp 2618 and ref. cited therein.) Iminium ions IV and V for the aldolization appear to lie near the energy maximum of this reaction. (E. J. Stamhuis, et al. *J. Org. Chem.* (1965): vol. 30, pp 2156; and P. Y. Sollenberger, et al. *J. Am. Chem. Soc.* (1970): vol. 92, pp 4261. We dislcose herein that haptens 1 and 2 which are capable of inducing catalytic antibodies for the former reaction, are also capable of inducing catalytic antibodies for the later. Haptens 1 and 2, by presenting a positive charge in the homobenzylic position of the aromatic nucleus (Ar), are shown to be analogs of the iminium and oxocarbonium ions III to V.

The catalytic aldolization cycle is also mechanistically closely related to the hydrolysis of enol ethers catalyzed by the antibodies. The condensation of amine 7 with the ketone to form enamine 9 is a step by step mechanistic reversal of the hydrolysis of 5. The key aldol addition of 9 to aldehyde 10 to form V is also shown to be similar to the rate determining protonation of the enol ethers. Finally, hydrolysis of the primary adduct to give 11 is also shown to be related to the hydrolysis of the oxocarbonium ion III. Accordingly, the primary amine 7 can serve as cofactor as it is regenerated by this hydrolysis.

The aldol addition of acetone to aldehyde 10a was chosen as model system. The aqueous enolization of acetone was a well documented reaction. (E. Tapuhi et al., *J. Am. Chem. Soc.* (1982): vol. 104, pp 5758; Y. Chiang et al., *J. Am. Chem. Soc.* (1984): vol. 106, pp 460; and Y. Chiang et al., *J. Am. Chem. Soc.* (1989): vol 111, pp 3977. The aldehyde was accessible in one step by palladium catalyzed coupling of 4-iodoacetanilide with methallyl alcohol and possessed good water solubility and a convenient UV active aromatic group for HPLC-analysis. The reaction proceeded in aqueous buffer above pH 7 under apparent hydroxide catalysis, and was spontaneously catalyzed by amine 7. This observation was not surprising since a number of primary and secondary amines, in particular α-amino-acids and pyrrolidine, are known to catalyze aldol processes in water at neutral pH. Aldol condensations catalyzed by primary and secondary amines in water have been disclosed by several authors. (F. G. Fischer et al., *Ber.* (1931): vol. 64, pp 2825; W. Langenbeck et al., *Ber.* (1942): vol. 75, pp 951; T. A. Spencer, et al., *Tetrahedron Lett.* (1965): vol. 3889; and C. D. Gutsche et al., *J. Am. Chem. Soc.* (1967): vol. 89, pp 1235.) Retroaldol reactions have also been disclosed. (F. H. Westheimer et al. *J. Am. Chem. Soc.* (1938): vol. 60, pp 90; F. H. Westheimer et al., *J. Am. Chem. Soc.* (1941): vol. 63, pp 3283.) Decarboxylations have also been disclosed. (K. J. Pedersen, *J. Am. Chem. Soc.* (1938): vol. 60, pp 595; and K. Johnsson, *Nature* (1993): vol. 365, pp 530.) Proton exchange of aldehyde imines have also been disclosed. (J. Hine, et al. *J. Am. Chem. Soc.* (1966): vol. 88, pp 3367.) Amino-acid catalysis of an aldol process in non-aqueous medium have also been disclosed. (C. Agami, *Bull. Soc. Chim. Fr.* (1988): vol. 3, pp 499 and ref. cited therein.)

Antibody Catalysis

We disclose herein that when anti-1,2 antibodies are employed to catalyze the reaction using amine 7 as cofactor, the stereochemical outcome of the reaction is influenced. Due to the spontaneous catalytic activity of 7 in solution, the observation of antibody catalysis would require a specific activation of this cofactor upon binding to the antibody. Twenty-four anti-1 and twenty-two anti-2 antibodies were assayed for catalysis of the formation of 11a from 10a and acetone at pH 8.0 in the presence of amine 7. Three anti-1 and three anti-2 antibodies catalyzed the reaction. The catalytic activities were quantitatively inhibited by addition of hapten 12 (scheme 2), ensuring that the reactions were taking place specifically in the antibody combining site. Antibody 72D4 (anti-2) was characterized in detail.

Complementary measurements were carried out to confirm the specificity of this antibody-catalyzed reaction. BSA (bovine serum albumin), and three monoclonal antibodies raised against unrelated haptens were assayed for catalysis of the reaction. Without cofactor 7, a small rate enhancement was observed in these samples relative to buffer alone. This effect probably reflected the reactivity of surface lysine residues, which was expected as primary amines catalyzed the reaction. In contrast to the six catalytic anti-1,2 antibodies, none of these proteins was able to raise the reactivity of cofactor 7 for aldolization catalysis above its activity in solution. This clearly excluded that activation of 7 might arise from a non-specific adsorption on the protein surface. Two series of monoclonal antibodies raised against the closely related haptens 13 (14 antibodies) and 14 (26 antibodies) (Chart I), which were expected to have a good binding affinity for amine 7, also did not show any catalysis for the aldol reaction with cofactor 7, suggesting a very specific role for the quaternary piperidinium portion of haptens i and 2 in inducing catalysis. Furthermore, no catalytic activity was observed with antibody 72D4 (anti-2) without amine 7, confirming its essential role as cofactor. While other primary and secondary amines, including benzylamine, 4-acetamido-benzylamine, L-valine, L-proline, methylamine, dimethylamine, also catalyzed the aldol reaction, no catalysis by the antibody was observed when these were used as cofactor instead of 7. Finally, antibody 72D4 was obtained from three separate monoclonal cell growth batches and each was assayed at different stages of purification. The catalytic activity, which was directly proportional to the antibody concentration, was observed in all of the samples, consistently increased upon purification, and was always quantitatively inhibited by addition of hapten 12. These measurements clearly indicated that the observed catalysis arouse from the specific combination of antibody 72D4 and cofactor 7.

A further indication of the high specificity of this antibody-catalyzed process was provided by determining the stereochemical purity of the aldol product. A semi-preparative reaction was carried out with antibody 72D4 and aldehyde 10a (0.2 mL, 40 mM Ab 72D4, 300 mM 10a, 300 mM cofactor 7, 1% v/v acetone, pH 9.0, 20° C.). The aldol product 11a was isolated by reverse-phase HPLC after 25% conversion (vs. 1.8% in a control reaction under identical conditions without the antibody), and analyzed by HPLC on chiral columns. The aldol product consisted of a 1:2.8 mixture of (SS)-11a (>95% de) and (RS)-11a (65% de) (scheme 4). (SS)-11a is formed by a Cram selective addition to (S)-10a, while (RS)-11a is formed by an anti-Cram selective addition to (R)-10a. The antibody thus selectively catalyzed addition to the Si stereo face of the aldehyde, irrespective of the absolute configuration of the adjacent center, representing a case of reagent controlled stereoselection. (D. J. Cram et al., *J. Am. Chem. Soc.* (1952): vol 74, pp 5828; C. H. Heathcock et al., *J. Am. Chem. Soc.* (1983): vol. 105, pp 1667: and C. Heathcock, *Science* (1981): vol. 214, pp 395.)

The absence of kinetic resolution was consistent with the observation that a range of different aldehydes were accepted as substrates (see below).

Kinetic Characterization

The aldol reaction of 10a and acetone to 11a with amine 7 as cofactor was followed by direct measurement of the formation of 11a by reverse-phase HPLC. The observed background reaction was first order in acetone (0.5% to 10% v/v) and aldehyde 10a (100–2000 mM), and was also first order in catalyst, either the amine cofactor 7 (50–1500 mM) as free base or hydroxide. The corresponding rate constants are $k_{app}(7)$ (third order) and $k_{app}(OH^-)$ (second order) for the apparent rate constant for each process at different pH, and $k(7)$ and $k_{OH^-}$ are the third order rate constants for catalysis by amine 7 as free base and hydroxide, respectively (FIG. 1).

The antibody 72D4 catalyzed reaction followed simple Michaelis-Menten kinetics for each substrate and for the cofactor, at fixed concentrations of the two other substrates, confirming its enzyme-like behavior (table 1). The kinetic parameters give, for each substrate, the apparent dissociation constant ($K_M$) and apparent first order rate constant ($k_{cat}$) of the antibody-substrate complex under the reaction conditions. In each case this rate constant $k_{cat}$ is certainly lower than the maximum rate because the antibody active site is not fully saturated with the other substrates. For acetone and aldehyde 10a, the background $k_{uncat}$ is the second order rate constant of their apparent bimolecular reaction, catalyzed by both hydroxide and amine 7 ([7]=0.2 mM and 0.4 mM, respectively). The rate acceleration $k_{cat}/k_{uncat}$ (123M and 102M) represents the apparent effective molarity of this reaction in the antibody active site. For cofactor 7, the first order background rate constant $k_{uncat}$ reflects the catalytic effect of amine 7 alone on the reaction, and the rate acceleration $k_{cat}/k_{uncat}$ (950) measures the specific activation of this cofactor upon binding to the antibody.

A number of other aldehydes 10b–10e, with different placement and substitution of the aromatic group, were also accepted as substrates (scheme 4). Apparent first order Michaelis-Menten kinetics were observed with each of these substrates for both the aldehyde and the cofactor 7 (table 2, FIG. 2). The tolerance for the aldehyde structure suggested that aldehyde binding was not taking place in the aromatic binding site of the antibody and was non-specific, in agreement with the absence of a designed binding site for this substrate.

While the concentrations of the amine cofactor 7 and acetone were in the range of their apparent Michaelis-Menten constants under typical assay conditions (table 1), the concentration of aldehyde was well below its $K_M$. The antibody-catalyzed reaction could thus be considered, kinetically, as a bimolecular reaction between a hypothetical antibody-acetone-amine complex, presumably the antibody-bound enamine 9, and the aldehyde (scheme 3). Under these conditions (200 mM fixed aldehyde 10a), the 72D4 -catalyzed reaction followed a random bimolecular model for amine 7 and acetone (scheme 5). (I. H. Segel, *Enzyme Kinetics;* John Wiley & Sons, New York, 1975, p.273–283.) The values obtained are $K_M(7) =45$ mM, $K_M$(acetone)=19 mM, $\alpha=26$, and $k_{cat}=0.014$ $M^{-1}s^{-1}$ at pH 8.0. This compares to $k_{app}(7)=3.8\times10^{-5}$ $M^{-2}s^{-1}$ for the background reaction catalyzed by amine 7, and $k_{app}(OH^-)=1.2\times10^{-8}$ $M^{31}$ $^1s^{-1}$ for the background reaction of acetone with aldehyde 10a, which is hydroxide catalyzed, at pH 8.0 (see FIG. 1). Formation of the corresponding $\alpha, \beta$-unsaturated ketone 15, which accounted for approximately 12% of the background reaction, was not measurably catalyzed by the antibody. Catalysis was also measured at pH 9.0, giving $K_M(7)=95$ mM, $K_M$(acetone)=120 mM, $\alpha=6.2$, and $k_{cat}=0.053$ $M^{-1}s^{-1}$, comparing to $k_{app}(7)=1.2\times10^{-4}$ $M^{-2}s^{-1}$ and $k_{app}(OH^-)=1.3\times10^{-7}$ $M^{-1}s^{-1}$ respectively. The rate enhancement for the antibody-catalyzed reaction over the background reaction catalyzed by 7 alone is given by the effective molarity, $k_{cat}/k_{app}(7)=370M$ at pH 8.0, and $k_{cat}/k_{app}(7)=440M$ at pH 9. These numbers compare the reactivities of the antibody-amine-acetone complex with amine plus acetone in solution, towards aldehyde 10a at 200 mM concentration.

Scheme 5.

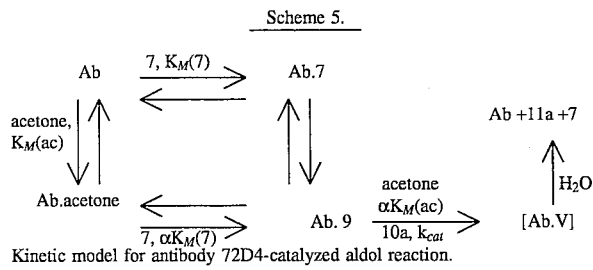

Kinetic model for antibody 72D4-catalyzed aldol reaction.

Reaction Mechanism

Further interpretation of the observed kinetic parameters required a more detailed understanding of the reaction mechanism. We have mentioned that amine 7 alone spontaneously catalyzed the reaction. The true catalytic role of this cofactor was first confirmed by a preparative scale synthesis. Thus, a solution of 0.1M aldehyde 10a and 0.1M amine 7 in buffer at pH=8.0 containing 10% acetone was heated at 80° C. for 5 hours, after which approximately 75% of the aldehyde was consumed. Under the same conditions, a control reaction in buffer at pH 8.0 without amine 7 gave less than 2% reaction. The product isolated from the amine catalyzed reaction (69% yield) consisted of a 1:2 mixture of the aldol 11a and enone 15 (Chart I). The formation of 15 was most probably caused by the dehydration of 11a at elevated temperature. This product was formed only in minor amount at room temperature and not at all in the antibody-catalyzed reaction. The unreacted aldehyde 10a was also recovered (15% yield). Most significantly, amine 7 was recovered unchanged (90% isolated).

Figure 3:
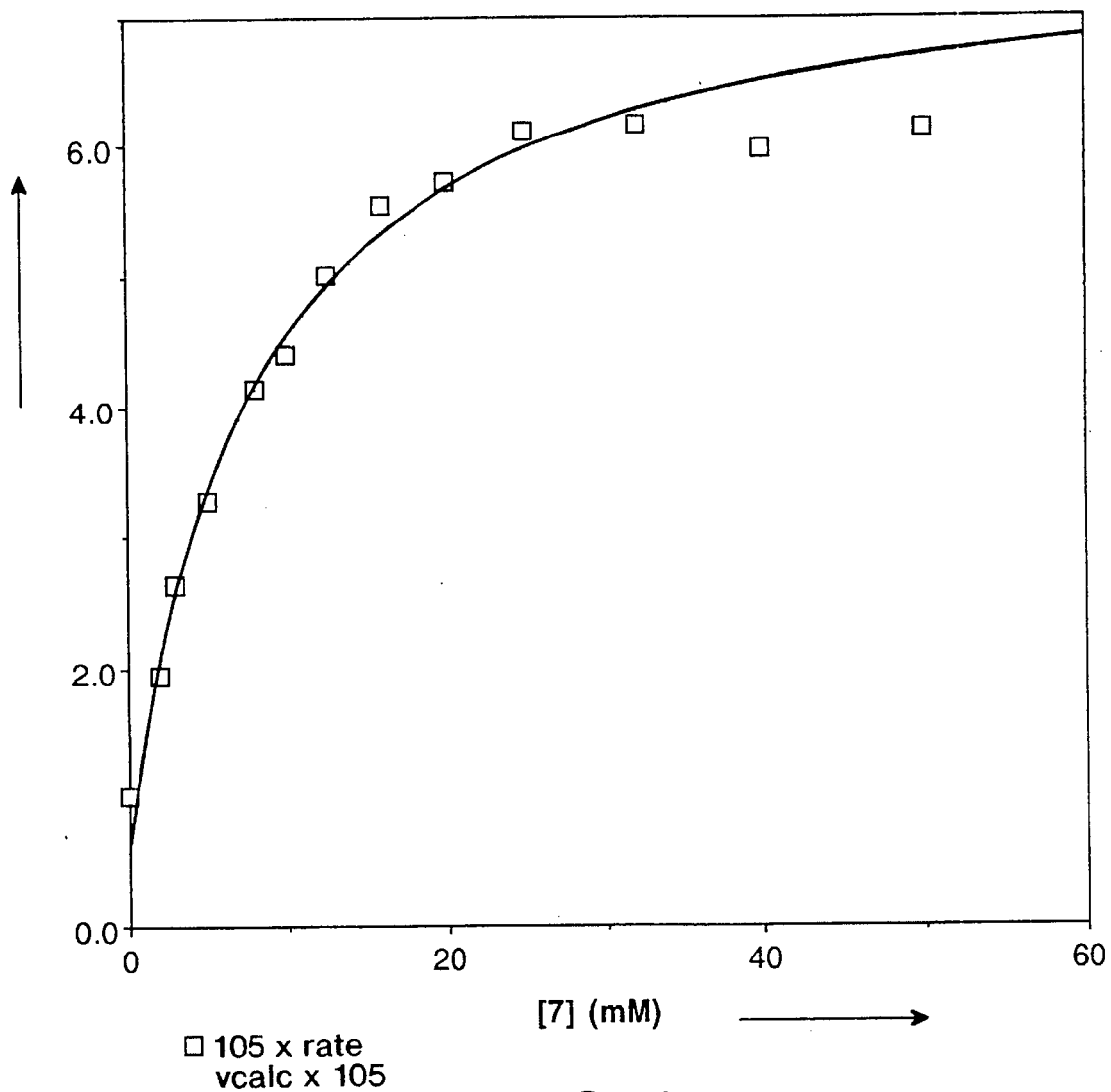
FIG. 3 illustrates the that the aldol reaction is first order in amine 7 at millimolar concentration, but displays apparent saturation kinetics at higher cofactor 7 concentrations.

Although the aldol reaction was first order in amine 7 at millimolar concentration, apparent saturation kinetics were observed for the initial rate of aldolization at higher cofactor 7 concentrations (FIG. 3). As no trace of any condensation product of amine 7 with acetone could be detected by $^1$H-NMR up to 20% v/v acetone, the effect could not be ascribed to the equilibrium formation of a reactive enamine intermediate. However, $^1$H-NMR spectra of mixtures of 7 and 10a at pH 9 showed the formation of imine 16 (Chart I). The saturation in catalysis thus most probably reflected a diminution of the concentration of free aldehyde in solution due to the formation of 16. Analysis of the data according to this model gave an equilibrium constant $K_{16}$ =7.8 mM for the dissociation of this imine to amine 7 and aldehyde 10a.

$$[10a]T \times k_{net(7)} = k_{app(7)} \times [7] \times [10a],$$  Equation (1)

with [7]T=[7]+[16] and [10a]T=[10a]+[16]. Under the conditions of the measurement (250 mM 10a), [10a]<<[7], one has [7]=[7]T and [10a]=[10a]T−[16]. The dissociation constant of imine 16 is K16=[7]×[10a]/([10]T−[10a]), from which [10a]=K16×[10a]T/([7]+K16). Replacement of [10a] with this expression in equation (1) above gives the expression in the legend of FIG. 3. The value obtained is comparable to the published value of 11 mM for the dissociation constant of the imine of isobutyraldehyde and methylamine in water at 35° C.[18i] (J. Hine et al. *J. Am. Chem. Soc.* (1966): vol. 88, pp 3367.) The preparative scale procedure above was in fact carried out at elevated temperatures because no significant reaction was taking place at 20° C., and analysis of the starting reaction mixture at room temperature also showed formation of imine 16. Clearly, imine 16 was not an intermediate in the catalytic aldolization cycle with cofactor 7, and the use of high temperatures or high dilutions was necessary to prevent its formation.

In the case of the aldolase enzymes, the formation of an iminium intermediate between the ketone and the active site lysine residue, which is the first step in the catalytic cycle (scheme 1), was experimentally established by the isolation of derivatives of this iminium, either the corresponding secondary amine obtained by reduction with NaBH$_4$ in situ, or by reversible trapping with cyanide to form an aminonitrile. (D. J. Cash et al., *J. Biol. Chem.* (1966): vol. 241, pp 4290; and K. Brand et al., *Arch. Biochem. Biophys.* (1968): vol 123, pp 312.) In direct analogy, we treated a solution of amine 7 in buffer (pH 7 to 9) containing 1% v/v acetone with cyanide (0.2M). The unstable Strecker product 17 (Chart I) was rapidly formed ($t_{1/2}$=30 minutes at pH 9). This reaction involves rate determining dehydration of aminal 8 to form imminium IV (scheme 3), which is then rapidly trapped with cyanide. The formation of α-aminonitrile 17 thus established that iminium IV could form under the conditions of the aldol reaction. Remarkably, iminium IV could be directly observed as the major peak in the mass spectra of the α-aminonitrile.

Figure 4:
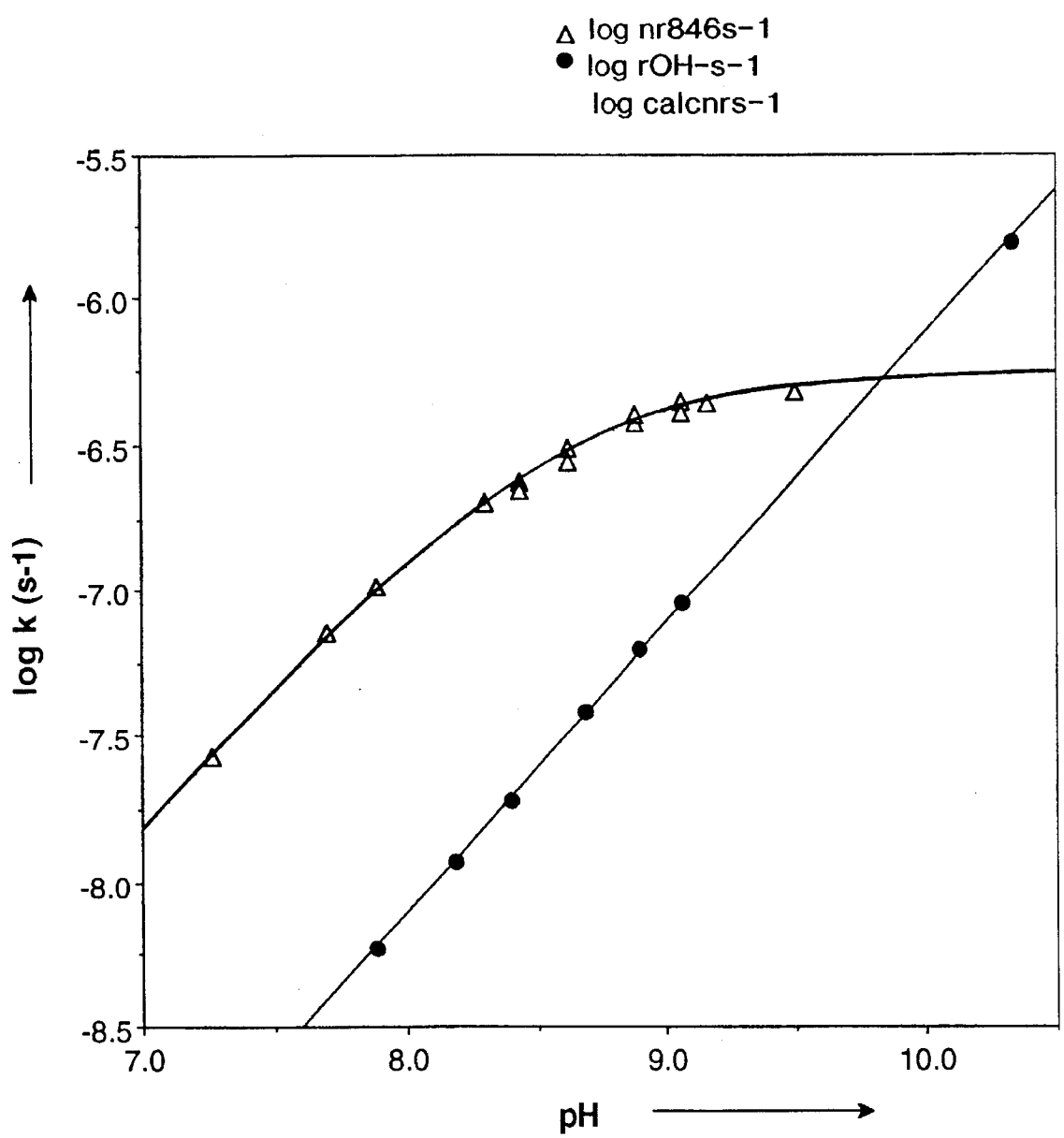
FIG. 4 illustrates the pH-profile for the formation of aldol 11a from acetone to 10a (0.2 mM) at 20° C. in 50 mM buffer (phosphate, bicine or triethanolamine), 100 mM NaCl, 5% v/v acetone. Triangles represent the pH-profile using amine 7 (1 mM) as a catalyst. Solid dots represent the pH-profile using N-methyl diethanolamine, a tertiary amine of similar $pK_a$, as a catalyst.

The aldol process consists of two consecutive reactions, removal of a proton from the α-carbon of the ketone, followed by coupling with the aldehyde. The relevance of iminium IV for the amine catalyzed aldolization was revealed by a kinetic study where both reactions were simultaneously followed in D$_2$O buffers at constant pD=9.0. The enolization of acetone was measured by following the exchange of H to D by $^1$H-NMR, and formation of the aldol product was monitored by HPLC as above. Cofactor 7 was compared with N-methyl diethanolamine, a tertiary amine of similar p$K_a$. Both amines showed comparable first order catalysis for proton exchange of acetone, but cofactor 7 also clearly showed a second order term (FIG. 4). While the amine 7 catalyzed aldol reaction was easily measurable above 0.1 mM, no catalysis of the aldol reaction was detected using N-methyl diethanolamine up to 75 mM. The rate of the aldol reaction catalyzed by amine 7 was also unchanged upon increasing the concentration of N-methyl diethanolamine.

The proton exchange catalyzed by N-methyl diethanolamine is the general-base catalyzed formation of the acetone enolate. The observation that this tertiary amine fails to catalyze the aldolization itself shows that the reaction is a specific base-catalyzed process involving rapid pre-equilibrium formation of the acetone enolate, followed by rate determining coupling with the aldehyde. (For mechanistic studies on the aldol reaction see J. P. Guthrie, *J. Am. Chem. Soc.* (1991): vol. 113, pp 7249 and ref. cited therein.) Aldolization catalysis by the primary amine 7 then must proceed via a different intermediate, which is likely enamine 9 (scheme 3). The second order term in the proton exchange probably represents general-base catalyzed formation of this enamine from iminium IV by the free amine 7. This interpretation, which is strongly supported by the isolation of aminonitrile 17 above, is consistent with previous studies on aldol and proton exchange reactions catalyzed with primary and secondary amines.[18] Although a second order term in the aldolization kinetics could be masked by the saturation effect caused by formation of imine 16, the fact that the amine 7 catalyzed aldolization was not accelerated by the general base N-methyl diethanolamine shows, as for the reaction via the acetone enolate, that the reaction involves rapid pre-equilibrium deprotonation of iminium IV followed by rate determining aldol addition of enamine 9 to the aldehyde. As the concentration of enamine 9 in solution should be directly proportional to the concentrations of the primary amine 7 and acetone, this scheme is fully compatible with the kinetic data which show first order in amine 7 as free base, acetone, and aldehyde.

Although the pKa of enamine 9 is expected to be different from that of the free amine 7, a simple formulation of the chemical equilibrium relating the two compounds shows that the only other terms involved are acetone and water: 7+acetone−H$_2$O=9. As far as the activities of acetone and water are pH independent, the ratio 7/9 is also pH independent, so that the pH profile of the amine catalyzed aldol reaction, which is kinetically determined by the concentration of enamine 9 and the aldehyde, displays the apparent pKa of the free amine. The p$K_a$ of amine 7 obtained by analysis of the pH-profile data (FIG. 1) indeed corresponds to the value obtained by titration (p$K_a$= 8.5).

The catalytic mechanism of the antibody 72D4 catalyzed aldol reaction should be similar to the solution chemistry of its essential cofactor. In order to establish the existence of iminium IV in the antibody 72D4-catalyzed reaction cycle, we thought a kinetic evidence that this intermediate was formed in the antibody active site. The formation of α-aminonitrile 17, which involves rate determining dehydration of the carbinolamine 8 to form iminium IV, (W. P. Jencks, *Catalysis in Chemistry and Enzymology*, McGraw Hill, New York, 1969, pp. 490–496) was indeed catalyzed by antibody 72D4 ($k_{cat}$=0.012 s$^{-1}$, $K_M$130 mM, $k_{uncat}$=3.8×10$^{-4}$ s$^{-1}$ at pH 9.0, 1% v/v acetone, 0.2M CN$^-$). Catalysis was quantitatively inhibited by hapten 12, showing that the reaction was taking place in the antibody combining site. Catalysis of imine formation has been reported earlier with antibodies. (T. Uno et al., *J. Am. Chem. Soc.* (1994): vol. 116, pp 1145; and A. G. Cochran et al., *J. Am. Chem. Soc.* (1991): vol. 113, pp 6670.) In the present case, catalysis of the formation of iminium IV in the active site of antibody 72D4 provides a strong evidence that aldolization catalysis by this antibody involves iminium IV and enamine 9 as intermediates.

Methods Section

A. Synthesis:

Reagents were purchased from Aldrich or Fluka. Solvents were A.C.S. grade from Fisher. All chromatographies (flash) were performed with Merck Silicagel 60 (0.040–0.063 mm). Preparative HPLC was done with Fisher Optima grade acetonitrile and ordinary deionized water using a Waters prepak cartridge 500 g installed on a Waters Prep LC 4000 system from Millipore, flow rate 100 mL/minutes, gradient+ 0.5%/minutes $CH_3CN$, detection by UV at 254 nm. TLC were performed with fluorescent Merck F254 glass plates. NMR spectra were recorded on a Brucker AM-300 MHz or AM-500 MHz instrument. Chemical shift d are given in ppm and coupling constant $^3J$ or $^2J$ in Herz. Infrared spectra were recorded on a Nicolet 510 FT-IR spectrometer, frequencies ñ given in $cm^{-1}$. MS, HRMS (high resolution mass spectra) and combustion analyses were provided by the Scripps Research Institute facility (Gary Szuidak).

N(hydroxyethyl)-4(aminomethyl)-benzamide 7

Gaseous hydrochloric acid was hubled for 5 minutes through a suspension of 4-(aminomethyl)benzoic acid (20 mmol) in 100 mL of methanol, upon which it dissolved. After heating at reflux for 10 minutes a precipitate was formed which was filtered off and washed with diethyl ether to yield 2.5 g (12.4 mmols, 62%) of 4-carbomethoxy-benzylammonium chloride. A solution of 1.5 g of this compound in 10 mL ethanolamine was heated at 37° C. overnight. After removal of the solvent by vacuum destillation, the residue was dissolved in 300 mL water and treated with 50 g of Dowex $H^+(SO_3H)$. The resin was washed several times with water and 50% aq. methanol. Treatment of the resin with 5% aq. ammonia and yielded 1.0 g (5.15 mmol, 69%) of amine 7 as a yellow solid, m.p. 140°–143° C. A sample (approx. 100 mg) was further purified by preparative reverse-phase HPLC to give the pure trifluoroacetate salt as a colorless solid after lyophilyzation, the latter was used as cofactor.

$^1$H-NMR (500 MHz, $D_2O$, $7H^+TFA^-$): 7.83, 7.56 (2d, 2×2H, J=8.3); 4.26 (s, 2H); 3.78 (t, 2H, J=5.5); 3.55 (t, 2H, J=5.5).

$^{13}$C-NMR (125 MHz, $D_2O$, $7H^+TFA^-$): 171.6, 137.4, 135.4, 130.0, 128.9, 61.0, 43.6, 43.0.

$C_{10}H_{14}N_2O_2$, HRMS (M+H$^+$) calcd 195.1134, found 195.1130

IR (KBr): 3359, 3071, 2971, 2922, 2851, 2763, 1639, 1558, 1509, 1444, 1330, 1296, 1057, 962, 744, 643.

4-(3'-oxo-2'-methyl-prop-1'-yl)-acetanilide 10a 2.19 g (8.4 mmol) 4-iodo-acetanilide, 2 mL 2-methyl-2-propen-1-ol, 0.8 g $NaHCO_3$, and 5 mg palladium(II) dichloride in 5 mL N-methyl pyrrolidone were heated at 150° C. under argon for 1 hour. Binding is the primary driving force for catalysis in many antibody-catalyzed bimolecular reactions. After workup (ethyl acetate/water), the residue was purified by chromatography (100 g $SiO_2$, ethyl acetate/hexane 1.5:1, Rf=0.25) to give 1.4 g (6.8 mmol, 81%) of 10a as a colorless crystalline solid, m.p. 108°–109° C.

$^1$H-NMR (300 MHz, CDCl$_3$): 9.75 (s, 1H); 7.42, 7.14 (2d, 2×2H, J=7.2); 7.20 (s, 1H); 3.62 (dd, 1H, J=13.0, 5.7); 3.06 (dd, 1H, J=13.0, 5.5); 3.60 (m, 1H); 2.18 (s, 3H); 1.09 (d, 3H, J=7.0). $^{13}$C-NMR (125 MHZ, CDCl$_3$): 204.6, 168.7, 136.4, 134.6, 129.4, 120.2, 48.0, 36.0, 24.4, 13.1.

$C_{12}H_{15}NO_2$ HRMS (M+H$^+$) calcd 206.1181, found 206.1178

IR (KBr): 3285, 2950, 2800, 1730, 1662, 1612, 1557, 1513, 1412, 1371, 1326, 846, 773.

4-(3'-oxoprop-1'-yl)-acetanilide 10b

A solution of 4-iodo-acetanilide (0.9 g, 4.1 mmol) and palladium(II) dichloride (7 mg) in N-methyl-pyrrolidone (2 mL) with allyl alcohol (1 mL) and $NaHCO_3$ (500 mg) was heated at 150° C. under argon for 4 hours (additional 3 mg portions of $PdCl_2$ were added after each hour), diluted with ethyl acetate (100 mL) and washed with 100 mL aq. sat. $NaHCO_3$. Chromatography (ethyl acetate/hexane 2:1, Rf=0.3) yielded 10b as a pale yellow solid (400 mg, 2.1 mmol, 51%). 120 mg of the compound were further purified by preparative reverse-phase HPLC to give 107 mg of pure 10b, m.p. 60°–62° C.

$^1$H-NMR (500 MHz, CDCl$_3$): 9.81 (s, 1H); 7.69 (hr. s, 1H); 7.41, 7.13 (2d, 2×2H, J=8.3); 2.91 (t, 2H, J=7.4); 2.76 (t, H, J=7.3); 2.15 (s, 3H). $^{13}$C-NMR (125 MHz, CDCl$_3$): 201.7, 168.5, 136.2, 128.8, 128.7, 120.3, 45.2, 27.4, 24.4.

$C_{11}H_{13}NO_2$: (M+H$^+$) calcd 192.1025, found 192.1030

IR (KBr): 3298, 2834, 2740, 1719, 1665, 1650, 1604, 1547, 1515, 1408, 1371, 1320, 1270.

3-(3'-oxo-2'-methyl-prop-1'-yl)-acetanilide 10c 0.5 g (2.3 mmol) 3-iodo-acetanilide, 0.6 mL 2-methyl-2-propen-1-ol, 0.2 g $NaHCO_3$, and 2 mg palladium(II) dichloride in 1.5 mL N-methyl pyrrolidone were heated at 140° C. under argon for 0.5 hour. After workup (ethyl acetate/water), the residue was purified by chromatography (100 g $SiO_2$, ethyl acetate/hexane 1:1, Rf=0.35) to give 270 mg (1.31 mmol, 57%) of 10c as a colorless solid, which was further purified by preparative RP-HPLC to give 200 mg of pure, colorless solid, m.p. 58°–60° C.

$^1$H-NMR (500 MHz, CDCl$_3$): 9.68 (s, 1H); 7.76 (br. s, 1H); 7.40 (m, 1H); 7.32 (br. d, 1H, J=8); 7.21 (t, 1H, J=8); 6.90 (d, 1H, J=8); 3.03 (dd, 1H, J=14, 6); 2.66 (qt, 1H, J=7, 7); 2.56 (dd, 1H, J=14, 8); 2.15 (s, 3H); 1.07 (d, 3H, J=7).

$^{13}$C-NMR (125 MHz, CDCl$_3$): 204.5, 168.7, 139.7, 139.1, 129.0, 124.8, 120.3, 117.9, 47.9, 36.5, 24.5, 13.2.

$C_{12}H_{15}NO_2$: HRMS (M+H$^+$) calcd 206.1181, found 206.1187; calcd C (70.22), H (7.37), N (6.82), found C (70.01), H (7.01), N (6.75) IR (film):3304, 2972, 2931, 1722, 1668, 1613, 1593, 1556, 1489, 1442, 1372, 1319, 1266.

3-(3'-oxoprop-1'-yl)-acetanilide 10d

A solution of 3-iodo-acetanilide (2.0 g, 7.7 mmol) and palladium(II) dichloride (5 mg) in N-methyl-pyrrolidone (3 mL) with allyl alcohol (2 mL) and $NaHCO_3$ (800 mg) was heated at 160° C. under argon for 1 hour (one additional 5 mg portion of $PdCl_2$ was added 10 minutes). After workup (water/ethyl acetate), chromatography (ethyl acetate/hexane 2:3 to 1.5:1) yielded 10d as a crystalline colorless solid (660 mg, 3.4 mmol, 45%), m.p. 53°–55 ° C. A 60 mg portion of this product was further purified by preparative RP-HPLC for kinetic assays.

$^1$H-NMR (500 MHz, CDCl$_3$): 9.77 (s, 1H); 8.0 (br. s, 1H); 7.41 (br. s, 1H); 7.31 (br. d, 1H, J=8); 7.20 (t, 1H, J=8); 6.91 (d, 1H, J=8); 2.89 (t, 2H, J=7 Hz); 2.74 (t, 2H, J=7 Hz); 2.14 (s, 3H).

$^{13}$C-NMR (125 MHz, CDCl$_3$): 201.7, 168.8, 141.2, 138.2, 129.0, 124.0, 119.7, 117.8, 45.0, 27.9, 24.4.

C$_{11}$H$_{13}$NO$_2$: HRMS (M+H$^+$) calcd 192.1025, found 192.1017; calcd C (69.09), H (6.85), N (7.33), found C (68.91), H (6.61), N (7.37)

IR (film): 3306, 3147, 3084, 2930, 2826, 2728, 1722, 1667, 1651, 1614, 1556, 1488, 1443, 1371, 1319, 1268.

3-(1'-oxo-2'-methyl-pent-5'-yl)-acetanilide 10e

A solution of aldehyde 10c (110 mg, 0.58 mmol) in 50% aq. ethanol (17 mL) containing 1 mL of propionaldehyde was treated with 10 drops of 2N NaOH. After 1 hour, the reaction was complete by TLC. Workup (ethyl acetate/1N HCl) followed by preparative RP-HPLC gave pure 3-(1'-oxo-2'-methyl-pent-2'-en-5'-yl)-acetanilide (80 mg, 0.35 mmol, 60%). Reduction with hydrogen (1 atm, Pd/C catalyst) in ethanol (6 mL) and purification by preparative HPLC yielded 57 mg (0.24 mmol, 70%) of aldehyde 10e as a colorless oil.

$^1$H-NMR (500 MHz, CDCl$_3$): 9.58 (d, 1H, J=2); 7.75 (br. s, 1H); 7.38 (br. s, 1H); 7.30 (br. d, 1H, J=8); 7.20 (t, 1H, J=8); 6.90 (d, 1H, J=8); 2.58 (t, 2H, J=7); 2.33 (hex d, 1H, J=7, 2); 2.15 (s, 3H); 1.76–1.58 (m, 2H); 1.38 (m, 1H); 1.08 (d, 3H, J=7).

$^{13}$C-NMR (125 MHz, CDCl$_3$): 205.3, 168.7, 142.8, 138.0, 128.8, 124.3, 119.8, 117.5, 46.1, 35.7, 29.9, 28.5, 24.5, 13.3.

C$_{14}$H$_{19}$NO$_2$: HRMS (M+H$^+$) calcd 234.1494, found 234.1483

IR (film): 3304, 2933, 1721, 1667, 1612, 1593, 1555, 1488, 1441, 1371, 1317.

Preparation of aldols 11a–11e: general procedure

The aldehyde (30 to 150 mg) was dissolved in acetone (1 mL) and water (4 mL) and NaOH (0.01 mL of saturated aq-soln.) was added. After completion of the reaction (approx. 1 hour at 20° C.), the solution was diluted with water, acidified to pH 2 with trifluoroacetic acid, and purified by preparative Rp-HPLC. Lyophilization of the pure fractions yielded the aldol products in approx. 60 to 90% yields.

11a: colorless solid, m.p. 62°–63° C.

$^1$H-NMR (500 MHz, CDCl$_3$): two stereoisomers in 1.4:1 ratio. Major isomer: 7.85 (s, 1H); 7.39, 7.08 (2d, 2×2H, J=8.4); 3.98 (m, 1H); 3.02 (d, 1H, J=3.0); 2.79 (dd, 1H, J=13.5); 2.67, 2.53 (2dd, 2×1H, J=17.5, 2.6); 2.39 (dd, 1H, J=13.5, 7); 2.17, 2.15 (2s, 2×3H); 1.72 (m, 1H); 0.87 (d, 3H, J=6.5). Minor isomer: 7.85 (s, 1H); 7.39, 7.07 (2d, 2×2H, J=8.3); 3.88 (m, 1H); 3.22 (d, 1H, J=3.0); 2.86 (dd, 1H, J=13.5, 4.6); 2.64, 2.59 (2dd, 2×1H, J=17.5, 9.7); 2.33 (dd, 1H, J=13.5, 9.5); 2.20, 2.15 (2s, 2×3H); 1.83 (m, 1H); 0.80 (d, 3H, J=6.8).

$^{13}$C-NMR (125 MHz, CDCl$_3$): Major isomer: 210.3, 168.7, 136.8, 135.8, 129.5, 120.0, 69.2, 47.4, 40.1, 38.7, 30.8, 24.3, 13.6. Minor isomer: 210.4, 168.7, 136.5, 135.8, 129.5, 120.0, 70.8, 46.6, 40.1, 37.9, 30.8, 24.3, 14.9.

MS (LSI): 264 (M$^{+H+}$)

IR (KBr): 3500–3300; 3287, 3247, 3183, 3120, 3066, 1708, 1648, 1558, 1535, 1521, 1503, 1492, 1459, 1409, 1370, 1325, 1270, 1041, 768.

C$^{15}$H$^{21}$NO$_3$ calcd C(68.41), H(8.04), N(5.32) found C(68.17), H(7.99), N(5.16)

11b: pale yellow oil $^1$H-NMR (500 MHz, CDCl$_3$): 8.14 (s, 1H); 7.37, 7.07 (2d, 2×2H, J=8.4), 4.01 (m, 1H); 3.41 (d, 1H, J=2.8); 2.71 (m, 1H); 2.61 (m, 3H); 2.14, 2.10 (2s, 2×3H); 1.74, 1.64 (2m, 2×1H).

$^{13}$C-NMR (125 MHz, CDCl$_3$): 210.0, 168.8, 137.6, 135.8, 128.7, 120.2, 66.6, 49.9, 37.9, 30.9, 30.7, 24.2.

C$_{14}$H$_{19}$NO$_3$ HRMS (M+H$^+$) calcd 250.1443, found 250.1450

IR (film): 3500–3200, 3123, 2935, 2916, 1710, 1667, 1604, 1535, 1434, 1370, 1070, 832, 733.

11c: colorless oil, 1.5:1 mixture of stereoisomers $^1$H-NMR (500 MHz, CDCl$_3$): major isomer: 8.17 (s, 1H); 7.35 (br. d, 1H, J=8); 7.32 (br. s, 1H); 7.17 (br. t, 1H, J=8); 6.87 (t, 1H, J=8); 3.97 (dt, 1H, J=10, 2); 3.10 (br. s, 1H); 2.75 (dd, 1H, 13, 6); 2.65–2.45 (m, 2H); 2.35 (dd, 1H, J=13, 8); 2.15 (s, 3H); 2.14 (s, 3H); 1.73 (m, 1H); 0.83 (d, 3H, J=7). minor isomer: 8.17 (s, 1H); 7.35 (br. d, 1H, J=8); 7.32 (br. s, 1H); 7.17 (br. t, 1H, J=8); 6.87 (t, 1H, J=8); 3.87 (ddd, 1H, J=9, 6, 2); 3.10 (br. s, 1H); 2.83 (dd, 1H, J=14, 5); 2.65–2.45 (m, 2H); 2.28 (dd, 1H, J=13, 9); 1.82 (m, 1H); 2.17 (s, 3H); 2.14 (s, 3H); 0.77 (d, 3H, J=7).

$^{13}$C-NMR (125 MHz, CDCl$_3$): major isomer: 210.3, 168.9, 141.7, 138.0, 128.7, 124.9, 120.5, 117.5, 69.2, 47.4, 39.9, 39.2, 30.7, 24.3, 13.6; minor isomer: 210.5, 168.9, 141.4, 138.0, 128.6, 125.0, 120.5, 117.5, 70.9, 46.6, 40.0, 38.4, 30.8, 24.3, 14.9.

C$_{15}$H$_{21}$NO$_3$: HRMS (M+H$^+$) calcd 264.1600, found 264.1593

IR (film): 3309, 3149, 2965, 2930, 1704, 1667, 1613, 1592, 1556, 1489, 1434, 1372, 1317, 1268, 1168, 1103, 1058, 964, 780, 702, 537.

11d: colorless oil $^1$H-NMR (500 MHz, CDCl$_3$): 7.70 (br. s, 1H); 3.76 (br. s, 1H); 7.32 (br. d, 1H, J=8); 7.20 (t, 1H, J=8); 6.93 (d, 1H, J=8); 4.01 (m, 1H); 3.25 (br. s, 1H); 2.75 (m, 1H); 2.64 (m, 1H); 2.61 (m, 2H); 2.16 (s, 3H); 2.15 (s, 3H); 1.77 (m, 1H); 1.66 (m, 1H).

$^{13}$C-NMR (125 MHZ, CDCl$_3$): 210.1, 168.6, 142.7, 138.0, 128.9, 124.4, 119.9, 117.5, 66.6, 49.9, 37.7, 31.6, 30.7, 24.5.

C$_{14}$H$_{19}$NO$_3$: HRMS (M+H$^+$) calcd 250.1443, found 250.1432

IR (film): 3306, 2928, 1704, 1667, 1612, 1592, 1556, 1489, 1434, 1371, 1319, 1168, 1072, 786, 699.

11e: colorless oil, 2:1 mixture of stereoisomers $^1$H-NMR (500 MHz, CDCl$_3$): major isomer: 7.62 (hr. s, 1H); 7.35 (br. s, 1H); 7.30 (br. d, 1H, J=8); 7.20 (t, 1H, J=8); 6.91 (d, 1H, J=8); 3.96 (dt, 1H, J=9, 3); 2.56 (m, 4H);, 2.18 (s, 3H); 2.15 (s, 3H); 1.66 (m, 1H); 1.58 (m, 1H); 1.49 (m, 2H); 1.16 (m, 1H); 0.88 (d, 3H, J=7); minor isomer: 7.62 (br. s, 1H); 7.35 (br. s, 1H); 7.30 (br. d, 1H, J=8); 7.20 (t, 1H, J=8); 6.91 (d, 1H, J=8); 3.88 (m, 1H); 2.19 (s, 3H); 2.15 (s, 3H); 1.66 (m, 1H); 1.58 (m, 1H); 1.49 (m, 2H); 1.16 (m, 1H); 0.87 (d, 3H, J=7).

$^{13}$C-NMR (125 MHz, CDCl$_3$): Major isomer: 210.4, 168.5, 143.4, 137.8, 128.8, 124.4, 119.8, 117.3, 70.4, 47.1, 37.7, 35.9, 32.1, 30.8, 28.9, 24.5, 14.2; Minor isomer: 210.4, 168.5, 143.4, 137.8, 128.8, 124.4, 119.8, 117.3, 71.1, 46.3, 37.8, 35.9, 31.7, 30.8, 28.7, 24.5, 14.9.

$C^{17}H_{25}NO_3$ HRMS (M+H$^+$) calcd 292.1913, found 292.1910

IR (film): 3306, 2932, 1704, 1668, 1613, 1592, 1556, 1488, 1440, 1371, 1318, 1167, 1065, 792, 699.

Preparative scale reaction with aldehyde 10a and amine 7

Aldehyde 10a (164 mg, 0.8 mmol, final concentration 0.1M) was dissolved in 8 mL of 50 mM bicine buffer pH=8.0, 0.1M amine 7 and 0.1M NaCl. After addition of 0.16 mL of acetone, the solution was heated at 80° C. for 5 hours, then cooled to room temperature and neutralized to pH 6.6. Purification by preparative reverse-phase HPLC as above yielded amine 7 (222 mg, 0.72 mmol, 90% recovery), aldol 11a (46 mg, 0.18 mmol, 23%), α, β-unsaturated ketone 15 (91 mg, 0.37 mmol, 46%) and recovered aldehyde 10a (25 mg, 15%). 15, colorless solid, m.p. 57°–58° C.

$^1$H-NMR (500 MHz, CDCl$_3$): 7.58 (s, 1H); 7.42, 7.06 (2d, 2×2H, J=8.3); 6.73 (dd, 1H, J=16, 7); 5.98 (d, 1H, J=16); 2.69 (m, 1H); 2.58 (m, 2H); 2.22, 2.16 (2s, 2×3H); 1.05 (d, 3H, J=6.2).

$^{13}$C-NMR (125 MHz, CDCl$_3$): 198.9, 168.4, 152.5, 136.1, 135.3, 129.6, 129.4, 119.9, 41.8, 38.3, 26.9, 24.4, 18.7.

$C_{15}H_{19}NO_2$ HRMS calcd: 246.1494, found 246.1490, calcd C(73.44), H(7.81), N(5.71), found C(73.50), H(7.73), N(5.83).

IR (KBr): 3288, 3249, 1697, 1671, 1612, 1357, 1530, 1492, 1410, 1325, 1263, 985, 784.

Determination of the stereochemistry for 11a-isomers 0.2 mL of a buffered solution (50 mM bicine, 100 mM NaCl, pH 9.0) containing Ab 72D4 (40 mM), aldehyde 10a (300 mM), amine 7 (300 mM) and 1% v/v acetone, was incubated at 20° C. for 10 days, which gave 25% conversion to the aldol product 11a. Two similar solutions, one without the antibody and one with antibody 72D4 and 250 mM of hapten 12, gave only 1.8% product formation under these conditions.

The aldol product was isolated by RP-HPLC and analyzed on chiral HPLC columns (3/1 hexane/isopropanol, 1.0 mL/minutes) as follows: 11a separated on chiracell AS: $t_R$((RS)-11a)=23.3 min, , $t_R$((SR)-11a)=25.0 minutes, $t_R$=S*S*)11a)=28.9 minutes; the peak at $t_R$=28.9 minutes was collected and separated on chiracell OJ: $t_R$((SS)-11a)=11.7 min, $t_R$((RR)-11a)=16.1 minutes.

The stereochemistry of the individual stereoisomers of aldol 11a was assigned as follows: a) configuration at the methyl group: by reaction in 85% H$_3$PO$_4$ (20° C. 2 h) each isolated 9a isomer gave cleanly and without racemization one of the enantiomers of the corresponding α, β-unsaturated ketone 15. This product was isolated by RP-HPLC and analyzed on chiracell AS: $t_R$ ((R)-15)=19.1 min and $t_R$ ((S)-15) 21.9 minutes b) relative stereochemistry: Cram sense stereochemistry was attributed to the major stereoisomer ((S*S*)-11a) of the background reaction (stereoselection: 1.5:1) in analogy to the observation of Heathcock et al. on a similar system (ref. 19b). The absolute configuration was not determined. The numbers refer to isomeric ratios after correction for the background reaction.

α-aminonitrile 17

Amine 7 (30 mg of HPLC purified TFA salt) was dissolved in water (0.5 mL) and treated with acetone (0.02 mL) and NaCN (10 mg). The pH was adjusted to 9.0 and the solution incubated overnight at 20° C. The solution was then acidified to pH 2.0 with trifluoroacetic acid and purified by preparative HPLC. The isolated TFA salt of 11 was suitable for MS analysis. NMR-spectra were collected in a solution prepared as above in D$_2$O.

$^1$H-NMR (500 MHz, D$_2$O): 7.77, 7.47 (2d, 2×2H, J=8); 3.88 (s, 2H); 3.78 (t, 2H, J=5.5); 3.54 (t, 2H, J=5.5); 1.57 (s, 6H) .

$C_{14}H_{19}N_3O_2$: observed $C_{13}H_{18}N_2O_2$ (loss of HCN), HRMS (M+H$^+$) calcd 235.1447 , found 235.1453

$^{13}$C-NMR (125 MHz, D$_2$O): 170.0, 141.6, 133.4, 132.2, 127.0, 122.6, 114.7, 59.5, 51.0, 47.8, 25.3.

Detection of imine 16 in aqueous solutions

Imine 16 forms spontaneously in buffered solution of amine 7 in water at basic pH, and can be detected by RP-HPLC ($t_R$=11.5 minutes conditions of 10a in table 3). The Mass spectrum of a 50 mM solution of 7 and 10a buffered at pH=9.0, with 10% acetonitrile as cosolvent, shows a major peak at 382. 16: $C_{22}H_{27}N_3O_7$, HRMS (M+H$^+$): calcd 382.2131, found 382.2129. In D$_2$O at pD 9.0, a mixture of 10 mM 7 and 5 mM 10a, consists of a 1:3:3 equilibrium mixture of imine 16, aldehyde 10a and its corresponding hydrated form (gem-diol). $^1$H-NMR (300 MHz, D$_2$O): 10a: 7.26, 7.22 (2d, 2×2H, J=8); 3.00 (dd, 1H, J=14, 7); 2.66 (dd, 1H, J=14, 8); 2.15 (s, 3H); 1.90 (m, 1H); 1.00 (d, 3H, J =7); visible signals forgem-diol: 2.83 (dd, 1H, J=14, 6); 2.38 (dd, 1H, J=14, 9); 0.80 (d, 3H, J=7); for 16: 7.58, 7.16, 7.10, 6.95 (4d, 4×2H, J=8); 4.55, 4.25 (2d, 2×1H, J=12); 1.08 (d, 3H, J=7).

B. Kinetic Measurements

Aldehydes 10a–10e were used as 25 mM stock solutions in 1:1 acetonitrile/water of the RP-HPLC purified samples. Cofactor 7 was used as 25 mM stock solution in pure water of the RP-HPLC purified trifluoroacetate salt. Antibody 72D4 was purified to homogeneity (SDS PAGE) by ion exchange and Protein G chromatography as described before,[4a] at 8–12 mg/mL stock solutions in either bicine (50 mM, pH 8.0) or phosphate (50 mM, pH 7.4) with 100 mM NaCl.

Assay Setup

Figure 2:
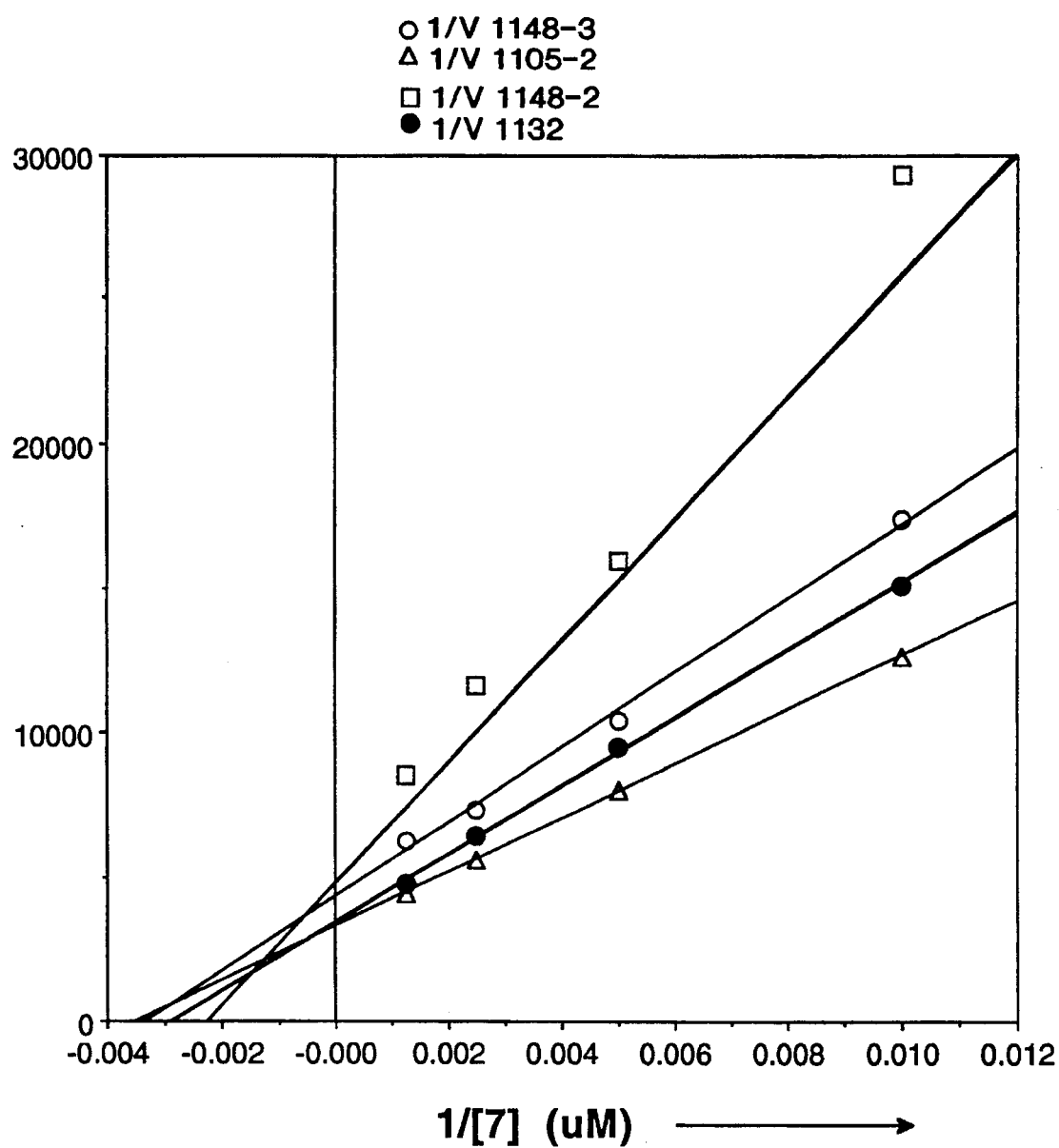
FIG. 2 illustrates a double reciprocal plot of the initial rate for antibody catalyzed formation of aldols 11b–e using each of the aldehydes 10b–10e listed in scheme 4 as substrates (0.2 mM) with acetone and amine 7 as a cofactor.

The setup for the kinetics of FIG. 2 is representative: a stock solution (1.8 mL) containing the antibody (11.1 mM) and acetone (1.11% v/v) in 50 mM bicine, 100 mM NaCl, pH 8.0 was separated into four portions of 400 mL. To each was added 3.6 mL of a 25 mM stock solution of each of the aldehydes 10a to 10d. Each 400 mL portion was further separated into four 90 mL portions and 10 mL of solutions of amine 7 in 50 mM bicine, 100 mM NaCl (1 mM, 2 mM, 4 mM, 8 mM) were added. Finally, 50 mL of each 100 mL sample was added to 0.5 mL of a 25 mM stock solution of hapten 12 in water. In each manipulation, the samples were vigorously shaken using a Vortex shaker to ensure homogeneity. The solutions obtained contained 200 mM of each aldehyde, 100, 200, 400 and 800 mM of amine 7, 10 mM antibody 72D4, and 1% v/v acetone in the buffer with or without 250 mM of hapten 12, and were in 0.5 mL plastic eppendorf tubes. These samples were incubated at 20° C. in a closed box containing 1% v/v acetone in water, to prevent evaporation of the acetone. The samples with antibody plus inhibitor were used for the uncatalyzed reaction, and the samples with antibody only for the catalyzed reaction, under each concentration conditions.

HPLC Assays

Product formation below 5% conversion versus starting material was followed over time by reverse-phase HPLC using a 5 mM, 300 A poresize C-18 silica column (0.45×22 cm) under isocratic elution conditions with acetonitrile/water mixture at 1.5 mL/min (table 3), detection by UV at 250 nm. The signal was recorded on a digital integrator.

TABLE 3

RP-HPLC conditions for the analysis of the aldol reactions of aldehydes 10a–10e.

| substrate | % A | % B | | |
|---|---|---|---|---|
| | minutes | | $t_R$ minutes | |
| $t_R$(aldol) | (0.1% TFA in $H_2O$) | | (50/50 $CH_3CN/H_2O$) | |
| 10a[a] | 75 | 25 | 20.5 | 24.4 |
| 10b[b] | 75 | 25 | 5.8 | 8.2 |
| 10c[c] | 70 | 30 | 16.4 | 26.5 |
| 10d[d] | 75 | 25 | 6.9 | 10.8 |
| 10e[e] | 50 | 50 | 13.4 | 8.8 |

[a]column: Microsorb-MV 86-203-C5;
[b]column: Vydac 218TP54.

Data Treatment

The rate in the inhibited antibody samples were used as measurements of the background reaction rate. The plot of this background rate versus amine 7 concentration was linear (4 points, $r^2>0.995$), and gave the hydroxide catalyzed reaction as the y-intercept, and the amine catalyzed reaction as the slope. The net catalytic rate in each antibody-only assay was obtained by subtracting the observed background rate in the corresponding inhibited sample. The net rates were used to derive the Michaelis-Menten constant $K_M$ and the maximum velocity $V_{max}$ from the Lineweaver-Burk plot of 1/V vs. 1/[S] (4 points, $r^2>0.993$). The catalytic constant $k_{cat}$ was obtained by dividing $V_{max}$ by the observed concentration of active catalytic sites in the antibody sample, which was determined by quantitative titration with hapten 12 as described before.[14a]

Formation of α-amino-nitrile 17

Conditions: 50 mM bicine, 0.2M NaCN, pH 9.0, 20° C. 50–1600 mM 7, 1% v/v acetone, 10 mM antibody 72D4. The reaction was initiated by addition of a concentrated stock solution of either amine 7 or buffered NaCN (no difference was noted). As above, pairs of identical antibody solutions, with and without hapten 12 as inhibitor, were used for measuring the background and catalyzed reaction rates, respectively. 15 mL samples were quenched at 45 sec intervals by mixing with 15 mL 0.5N TFA in water, immediately frozen, and later analyzed by RP-HPLC (C-18 as above, 92.5% $H_2O$, 7.5% $CH_3CN$, $t_R(17)=7.8$ minutes) against an internal standard (4-hydroxy-benzoic acid, $t_R=9.4$ minutes). A large injection peak caused by cyanide masked the peak for amine 7 ($t_R=3.4$ minutes) under these conditions. The background rate $k_{uncat}$ was derived from the inhibited samples (V vs. [S], 6 points, $r^2=1.0$). $K_M$ and $V_{max}$ were obtained from the Lineweaver-Burk plot of 1/V vs. 1/[S] as above (50, 100, 200, 400, 800, 1600 mM 7, 6 points, $r^2=0.98$).

Enolization of acetone in $D_2O$

Two 100 mM stock solutions of either amine 7 as TFA salt or N-methyldiethanolamine were adjusted at pD=9.0 (electrode reading 8.6) and diluted with 100 mM NaCl in $D_2O$ to obtain final concentrations of 10, 15, 20, 25, and 30 mM of the amine. The pD of all these solutions was 9.0 +/−0.05. Acetone-$H_6$ was added to make 1% v/v and the decrease of the integration of the acetone $^1$H-signal, versus the signals of the amines, was followed over time. The reaction was followed for 2 half-lives, and showed first order kinetics over that period. The rate of proton exchange at [amine]=0 was extrapolated from the rate measured with NaOD at pD=12.4. The first order rate constants reported in FIG. 4 are corrected for the exchange of one hydrogen.

Solutions were similarly prepared containing 0 or 2 mM 7, with 200 mnM 10a, 3% v/v acetone, and 25, 50 or 75 mM N-methyl diethanolamine at pD=9.0, and the rate of formation of aldol 11a was measured by RP-HPLC as above. The rate of aldolization observed was independent of the concentration of N-methyl-diethanolamine with both 0 and 2 mM 7.

Synthesis of Haptens 1 and 2

The synthesis of haptens 1 and 2 are illustrated in Schemes 6, 7, and 8. Details of these syntheses are provided as follows:

Scheme 6.

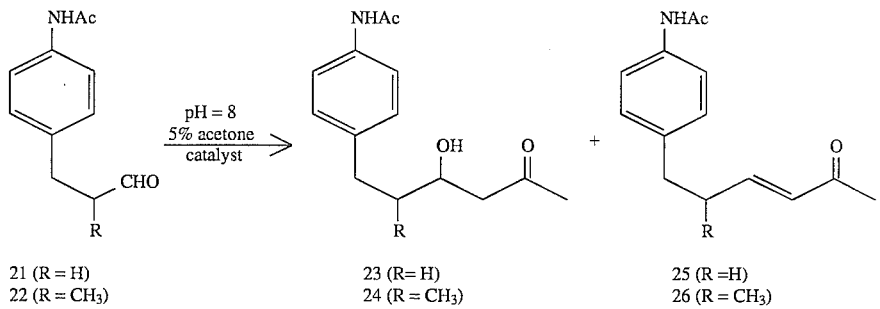

21 (R = H)
22 (R = CH3)

23 (R= H)
24 (R = CH3)

25 (R =H)
26 (R = CH3)

-continued
Scheme 6.
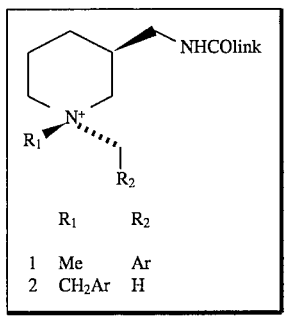
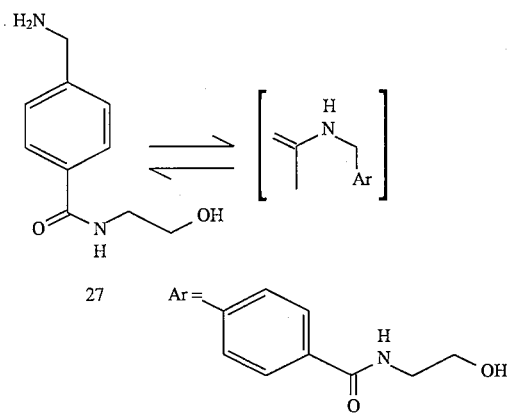
Scheme 7
Synthesis of haptens 1 and 2
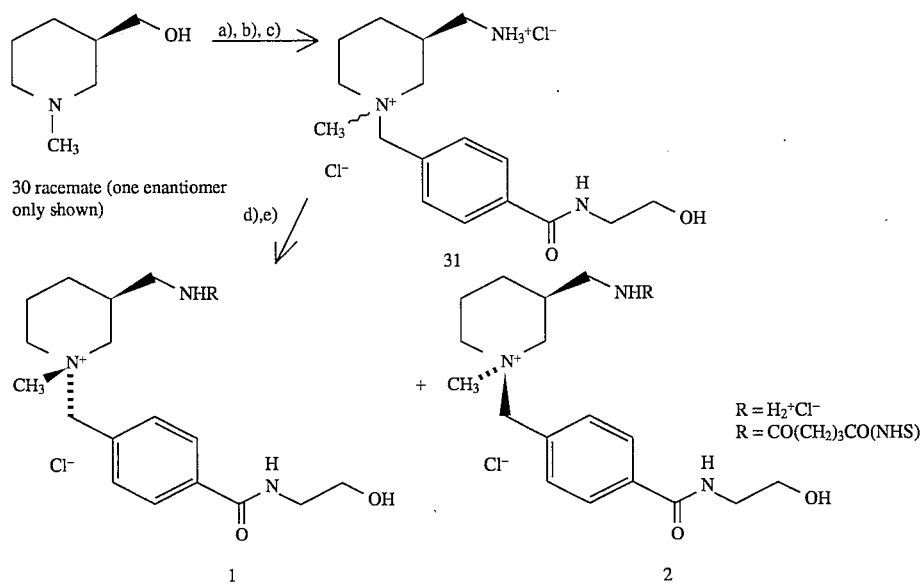
Scheme 8.
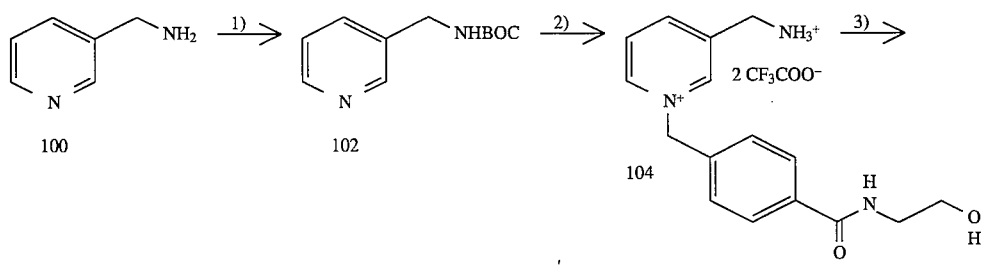

-continued
Scheme 8.

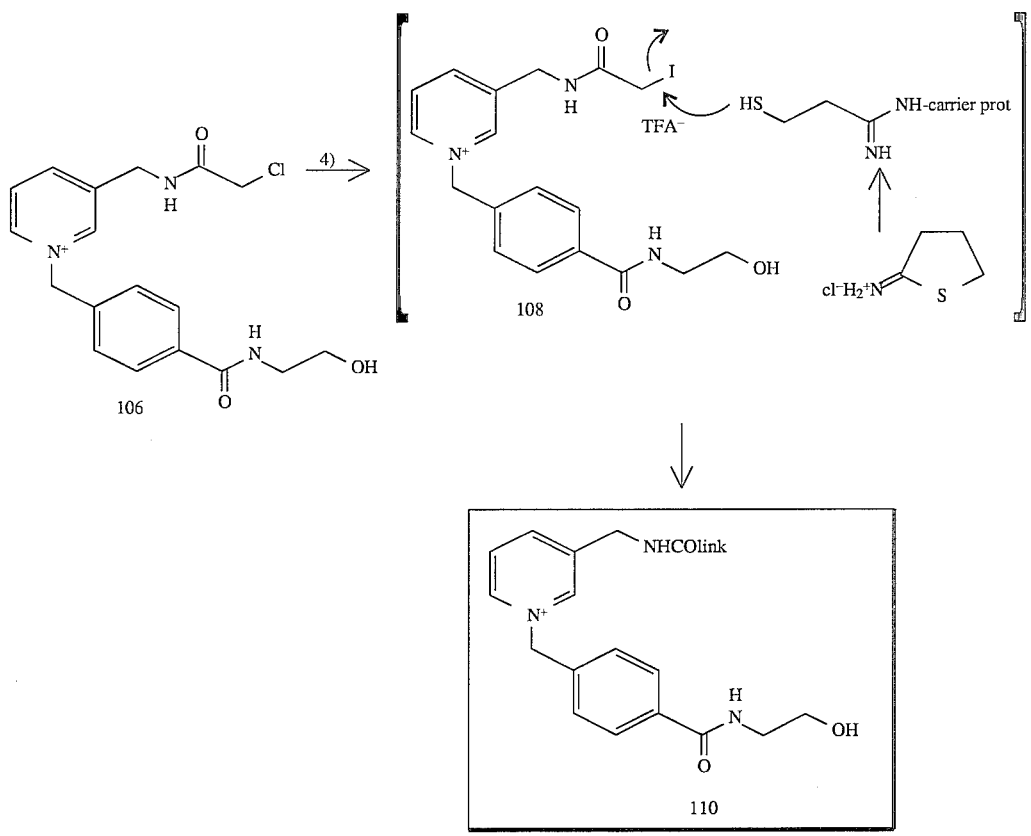

Preparation of compound 21

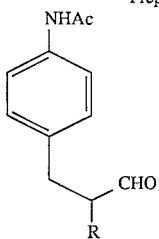

21 (R = H)
22 (R = CH₃)

Compound 21. Reaction of 4-iodo-acetanilide (1.0 equivalents) with allyl alcohol (1.2 equivalents), solid sodium bicarbonate (1.3 equivalents) and palladium (II) acetate (0.01 equivalents) in N-methyl-pyrrolidone (3.2 Molar) at 150° C. for 1 to 4 hours, followed by workup (HCl 0.5 Normal/ethyl acetate) and chromatography (hexane/ethyl acetate approximately 5:1), yields the desired aldehyde compound 21 as a colorless oil.

Preparation of compound 22

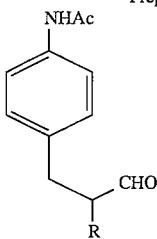

21 (R = H)
22 (R = CH₃)

Compound 22. Reaction of 4-iodo-acetanilide (1.0 equivalents) with 2-methyl-2-propen-1-ol (1.2 equivalents, from Aldrich company), solid sodium bicarbonate (1.3 equivalents) and palladium (II) acetate (0.01 equivalents) in N-methyl-pyrrolidone (3.2 Molar) at 150° C. for 1 to 4 hours, followed by workup (HCl 0.5 Normal/ethyl acetate) and chromatography (hexane/ethyl acetate approximately 5:1), yields the desired aldehyde compound 22 as a colorless oil.

Preparation of Compound 27

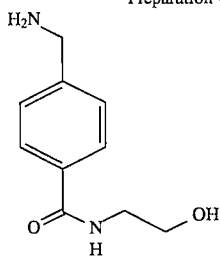

Compound 27. To a solution of 4-aminomethyl-benzoic acid (1.0 equivalents, from Aldrich company) is added a catalytic amount of (1 Molar) hydrochloric acid (0.10 equivalents) and is followed by the addition of ethanolamine (1.2 equivalents). The reaction is then allowed to stir for 1 to 4 hours and is quenched by sodium bicarbonate (0.5 equivalents). The solvent is removed via rotavaporation under reduced pressure and then resuspended in ethyl acetate and washed with water (1X), brine (1X) and dried over magnesium sulfate. After concentration, the product is purified by ion exhange on Dowex H+. All compounds give satisfactory $^1$H–, $^{13}$C-NMR, IR spectra and elemental analysis or high resolution MS data.

Synthesis of the pyridinium haptens 1 and 2, scheme 7.

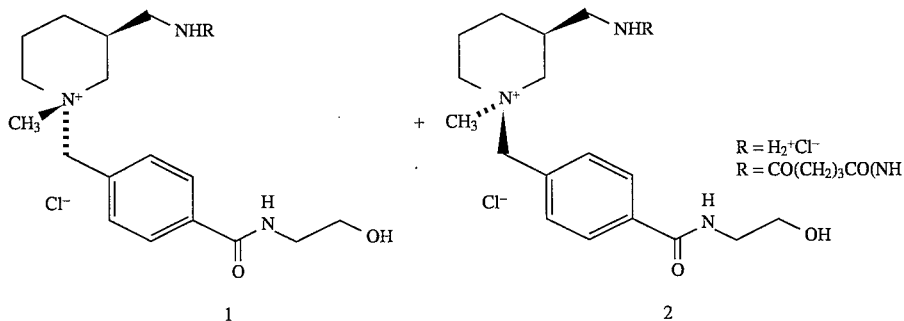

step a.) Formation of N-methyl-3-piperidinemethylazide intermediate. To a solution of N-methyl-3-piperidinemethanol (1.0 equivalents from Aldrich) in methylene chloride (0.10 Molar) is added mesyl chloride CH$_3$SO$_2$Cl (1.1 equivalents) at 0° C. to 10° C. and is stirred for 2 hours. Next, the reaction mixture is exposed to sodium azide (1.1 equivalents) and the reaction is then heated to 90° C. for 4 hours. The reaction is then quenched with water and subsequently washed in ethylacetate (0.01 Molar), water (2X), brine (1X) and dried over magnesium sulfate. The crude product is carried on to step b.

step b.) Formation of 4-(chloromethyl)-N -(2-hydroxyethyl)-benzamide. Procedure as adapted from experimental for compound 8 in Reymond et al. *J. Am. Chem. Soc.* 1993, 115, pg 3916. 4-(Chloromethyl)benzoic acid (1.0 equivalents, from Aldrich company) was suspended in methylene chloride (0.60M) and treated with oxalyl chloride (1.6 equivalents) with a Dimethyl formamide catalyst (0.1 equivalents) at 20° C. for 30 minutes. Evaporation of the solvent under vacuum left a crystalline residue which was dissolved in methylene chloride (0.70 equivalents) and treated with ethanolamine (1.4 equivalents). Workup (brine/ethyl acetate) followed by crystallization of the residue (ethanol/hexane) gave 4-(chloromethyl)-N-(2'-hydroxyethyl)benzamide as colorless crystals.

The 4-(chloromethyl)-N-(2'-hydroxyethyl)benzamide (1.2 equivalents) in water (0.70 equivalents) is heated with N-methyl-3-piperidinemethylazide (1.0 equivalents, formed in step a) and diisopropylethyl amine (1.2 equivalents) at 80° C. for 2 hours. Recrystallization from isopropyl alcohol and diethyl ether then gives the desired piperidinium-azide chloride salt.

steps c and d.) The piperidinium-2-methylazide chloride salt (1.0 equivalents) is then exposed to Lindlar's catalyst (0.10 equivalents—Palladium on calcium carbonate, poisoned with lead and purchased from Aldrich company) in methanol/water mix (1:1, 0.10 molar total) at 20° C. for 4 hours. The reaction mixture is then purified by FPLC and then separated by semi-prep. A final HPLC purification is then run twice to obtain two separate enantiomers with a combined yield of approximately 70%.

step e) The free amine hydrochloride salt of 1 or 2 (1.0 equivalents) is then suspended in dimethylformamide (0.10 molar) and cooled to –30° C. Diisopropylethylamine (1.2 equivalents) and then the succinyl chloride coupled to carrier proteins BSA or KLH (ClCO(CH$_2$)$_3$CO(NHS), 1.1 equivalents, which had been first thiolated with Traut's reagent according to standard procedures for an example see Reymond et. al. *J. Am. Chem. Soc.* 1993 115, 3909), are added and the reaction is allowed to stir for 1 hour. The reaction mixture is then purified by FPLC and then separated by semi-prep. A final HPLC purification is then run to obtain the desired hapten 1 or 2.

Synthesis of the pyridinium hapten 110 scheme 8

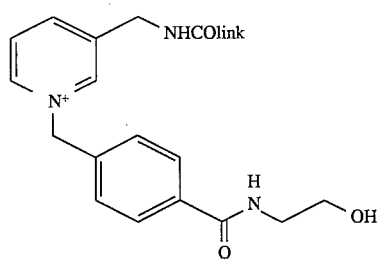

The synthesis was carried out from commercially available 3-(aminomethyl)-pyridine 100 in a four step sequence involving:

1) N-protection of the primary amine with a BOC protecting group as follows: 50 μL (0.49 mmol) of 3-(aminomethyl)-pyridine 100 in 1 mL of 4:1 acetonitrile/water was treated with 120 mg (1.1 eq.) of di-tert-butyl dicarbonate at 20° C. for 3 hours and directly purified by chromatography on silicagel (5% v/v methanol in CH$_2$Cl$_2$) to yield 102, 109 mg (>100%) of BOC-protected material;

2) alkylation of the pyridine nitrogen with N-(hydroxyethyl)-4-(chloromethyl)-benzamide and BOC deprotection as follows: 102 was treated with 110 mg of N(hydroxyethyl)-4-(chloromethyl)-benzamide (1 eq.) in 2 mL acetonitrile and 0.3 mL of saturated aqueous NaHCO₃ and 20 mg of NaI at 50° C. for 3 hours. The solvent was then removed by evaporation and the residue treated with 10:1 1N aqueous HCl/ acetonitrile at reflux for 5 min. After dilution with water (50 mL), purification by reverse-phase HPLC (C-18, gradient water+0.1% TFA to acetonitrile) yielded the bis-trifluoracetate 104;

3) Chloroacetylation as follows: The intermediate 104 was dissolved in 4 mL of acetonitrile and treated with 100 mg of solid NaHCO₃ and 150 mg of chloroacetic anhydride at 20° C. for 20 min. Purification by RP-HPLC as above gave the chloroacetamide 106 (207 mg, yellow oil);

4) Halogen exchange with NaI to form the iodoacetamide 108 as follows: Reaction of 85 mg 4 with 200 mg NaI in 2 mL acetonitrile for 3 h at 20° C. for three hours followed by RP-HPLC purification as above yielded 70 mg of the activated iodoacetamide 108.

The HPLC-purified hapten was then coupled to form 110 at the SH group of carrier proteins BSA and KLH, which had been first thiolated with Traut's reagent according to standard procedures for an example see Reymond et. al. *J. Am. Chem Soc.* 1993 115, 3909.

What is claimed is:

1. A catalytically active mixture comprising:
   a solvent,
   a catalytic antibody or antibody fragment admixed within said solvent, and
   a primary or secondary amine cofactor admixed within said solvent,
   said catalytic antibody having a catalytic activity dependent upon the presence of said primary or secondary amine cofactor for catalyzing a stereoselective aldolization reaction.

2. A catalytically active mixture as described in claim 1 wherein said primary or secondary amine cofactor has a $pK_a$ substantially equivalent to or lower than the $pK_a$ of benzylamine.

3. A catalytically active mixture as described in claim 1 wherein said catalytic antibody includes an epitope that binds a quaternary piperidinium hapten.

4. A catalytically active mixture as described in claim 3 wherein said primary or secondary amine cofactor is benzylamine.

5. A reaction mixture comprising:
   a solvent,
   a catalytic antibody or antibody fragment admixed within said solvent,
   a primary or secondary amine cofactor admixed within said solvent,
   a ketone admixed with said solvent, and
   an aldehyde admixed with said solvent,
   said catalytic antibody or antibody fragment displaying a catalytic activity in the presence of said primary or secondary amine cofactor for catalyzing a stereoselective aldolization reaction between said ketone and said aldehyde.

6. A reaction mixture as described in claim 5 wherein said primary or secondary amine cofactor has a $pK_a$ substantially equivalent to or lower than the $pK_a$ of benzylamine.

7. A reaction mixture as described in claim 5 wherein said catalytic antibody or antibody fragment includes an epitope that binds a quaternary piperidinium hapten.

8. A reaction mixture as described in claim 7 wherein said primary or secondary amine cofactor is benzylamine.

9. A reaction mixture as described in claim 8 wherein said ketone is acetone.

10. A method for identifying a catalytic antibody having a catalytic activity dependent upon a primary or secondary amine cofactor, the method comprising the following steps:

Step A: admixing the catalytic antibody, the primary or secondary amine cofactor, and one or more substrates; then Step B: monitoring the rate of conversion of substrate to product within the admixture of said Step A; while independently Step C: admixing the catalytic antibody and one or more substrates of said Step A without the primary or secondary amine cofactor; then Step D: monitoring the rate of conversion of substrate to product within the admixture of said Step C; and then Step E: comparing the rate of conversion of substrate to product in said Step B and D and identifying the catalytic antibody having the greater rate of a conversion in said Step B as compared to said Step D as having the catalytic activity dependent upon the primary or secondary amine cofactor.

* * * * *